United States Patent [19]
Hosoda et al.

[11] Patent Number: 5,506,111
[45] Date of Patent: Apr. 9, 1996

[54] METHOD OF IMMUNOLOGICAL ASSAYING OF HUMAN OSTEOCALCIN, REAGENT AND KIT THEREFOR, ANTIBODY TO HUMAN OSTEOCALCIN, HYBRIDOMA PRODUCING SAID ANTIBODY, AND METHOD OF PRODUCING IT

[75] Inventors: Kenji Hosoda, Kawagoe; Hitomi Honda, Hino; Takaharu Kubota, Hino; Yasuhiko Masuho, Hino, all of Japan

[73] Assignee: Teijin Limited, Osaka, Japan

[21] Appl. No.: 316,364

[22] Filed: Oct. 3, 1994

Related U.S. Application Data

[63] Continuation of Ser. No. 38,544, Mar. 29, 1993, abandoned, which is a continuation of Ser. No. 582,849, Oct. 10, 1990, abandoned.

[30] Foreign Application Priority Data

Feb. 10, 1989 [JP] Japan .................................. 1-255306
Oct. 2, 1989 [JP] Japan .................................. 1-30003

[51] Int. Cl.$^6$ .................................. G01N 33/53
[52] U.S. Cl. .................. 435/7.94; 435/7.9; 435/7.92; 435/975; 436/512; 436/518; 436/531; 436/547; 436/548; 530/388.1; 530/389.1; 530/391.1; 530/391.3
[58] Field of Search .................. 435/7.9, 7.92, 435/7.94, 7.95, 975; 436/512, 518, 531, 534, 547, 548; 530/388.1, 389.1, 391.1, 391.3

[56] References Cited

U.S. PATENT DOCUMENTS 4,438,208  3/1984  Deftos et al. .................. 436/542

FOREIGN PATENT DOCUMENTS

3842498A1  6/1989  Germany .
60-146154  8/1985  Japan .
1-160493  6/1989  Japan .

OTHER PUBLICATIONS

Principles of Biochemistry, 7th Edition, Smith et al, eds., (McGraw–Hill Book Co., New York, 1983), pp. 23–30.
Hosoda et al, "Sandwich Immunoassay for Intact Human Osteocalcin", Clin. Chem. 38/11:2233–2238 (1992).
Kanzaki et al, "Serum Prepeptide and Intact Molecular Osteocalcin in Normal Children and Children with Growth Hormone(GH)Deficiency: A Potential Marker of Bone Growth and Response to GH Therapy", J. Clin. Endocrinol. Metab., 75(4):1104–1109 (1992).
Harlow and Lane, Antibodies A Laboratory Manual, pp. 72–77 (Cold Springs Harbor Laboratory, 1988).
Grundberg et al, "Multiple Immunoreactive Forms of Osteocalcin in Uremic Serum", J. Clin. Invest., 77:1762–1767 (Jun. 1986).
Gundberg et al, J. Clin. Invest., 77: 1762–1767 (Jun. 1986).
Affinity Chromatography Principles & Methods, Pharmacia Laboratory Separation Division pp. 6–10 (1986).
Bullinski et al., "Peptide Antibodies: New Tools for Cell Biology", in *International Review of Cytology*, vol. 103, Academic Press, Inc., Orlando, FL, pp. 281–302 (1986).
Hopp et al., "Prediction of protein antigenic determination from amino acid sequences", *Proc. Natl. Acad. Sci.*, vol. 78, No. 6, pp. 3824–3828 (1981).
Geysen et al., "Cognitive Features of Continuous Antigenic Determinants", *Journal of Molecular Recognition*, vol. 1, No. 1, (1988), pp. 32–41.
Marc H. V. Van Regenmortel, "Which structural features determine protein antigenicity?", *TIBS* Jan. 1986, pp. 36–39.
Grimaux et al., Calcified Tissue International, vol. 48, Supplement 1991, p. A62, Abstract No. 232.
Koyama et al., Journal of Immunological Methods, vol. 139, pp. 17–23 (1991).
Patent Abstracts of Japan, vol. 12, No. 496 (C–555) (3343) 23 Dec. 1988 & JP–A–63 209 596, 31 Aug. 1988.
Tanaka et al., J. of Immunological Methods, "An Enzyme Immunoassay for Osteocalcin", vol. 94, pp. 19–24 (1986).

*Primary Examiner*—Toni R. Scheiner
*Assistant Examiner*—Susan C. Wolski
*Attorney, Agent, or Firm*—Wenderoth, Lind & Ponack

[57] ABSTRACT

A method of immunologically assaying intact human osteocalcin in a human assay sample is provided by using an antibody having an epitope in a region of an amino acid sequence 1 to 20 on the N-terminal side of human osteocalcin and an antibody having an epitope in a region of an amino acid sequence 36 to 49 on the C-terminal side of human osteocalcin. A reagent and a kit therefor are provided. Furthermore, a method of immunologically assaying the total amount of human intact osteocalcin in a human assay sample, and a reagent and a kit therefor are also provided. A monoclonal antibody and a polyclonal antibody are used for the assay. A process for producing these antibodies, and utilization of these antibodies is described.

13 Claims, 10 Drawing Sheets

FIG. 1

```
  1    2    3    4    5    6    7    8    9   10
H-Tyr-Leu-Tyr-Gln-Trp-Leu-Gly-Ala-Pro-Val- 11   12   13   14   15   16   17   18   19   20
  Pro-Tyr-Pro-Asp-Pro-Leu-Glu-Pro-Arg-Arg-

21
  Cys-OH
```

FIG. 2

```
 43   44   45   46   47   48   49
H-Arg-Arg-Phe-Tyr-Gly-Pro-Val-OH
```

FIG. 3

```
 35   36   37   38   39   40   41   42   43   44
H-Cys-Ile-Gly-Phe-Gln-Glu-Ala-Tyr-Arg-Arg- 45   46   47   48   49
  Phe-Tyr-Gly-Pro-Val-OH
```

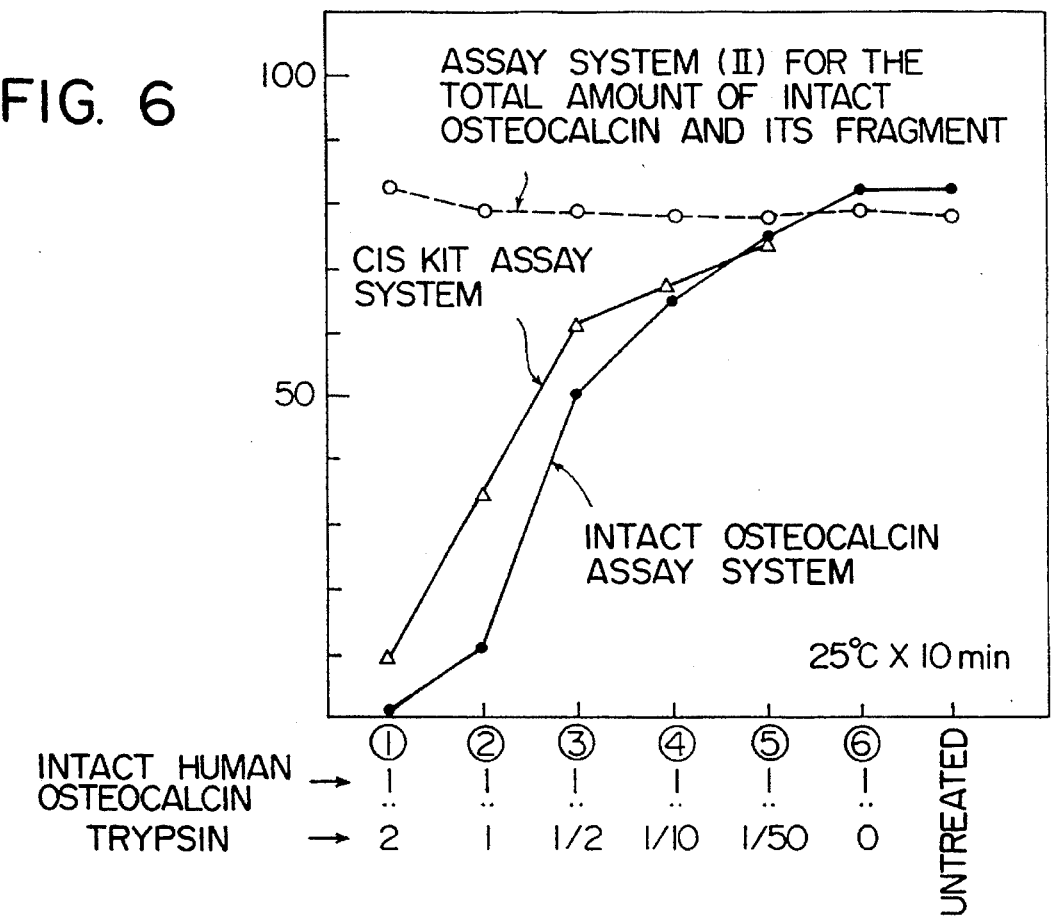
FIG. 6 STUDYING OF INTACT HUMAN OSTEOCALCIN AND ITS FRAGMENT
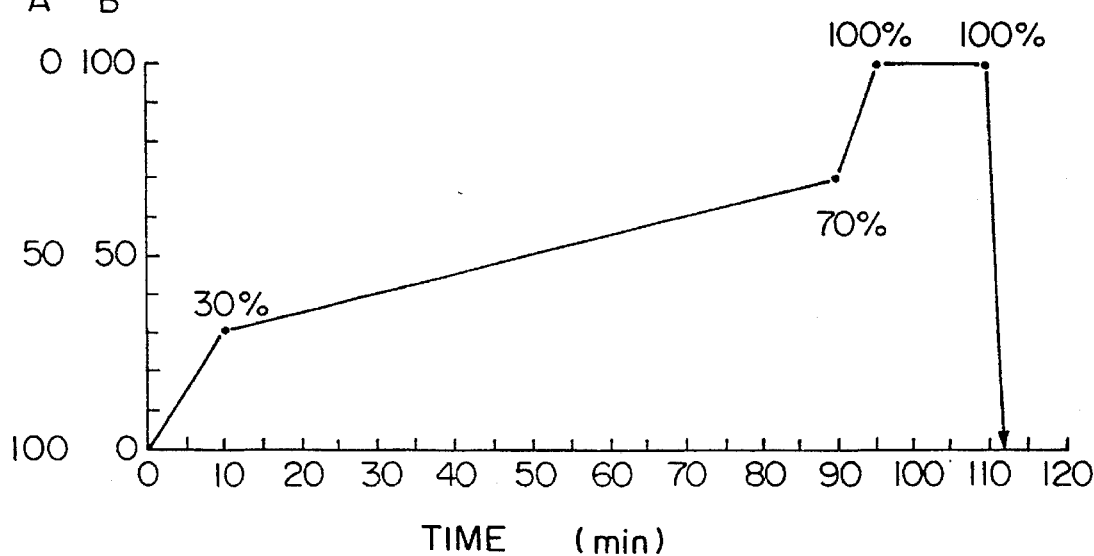
FIG. 7

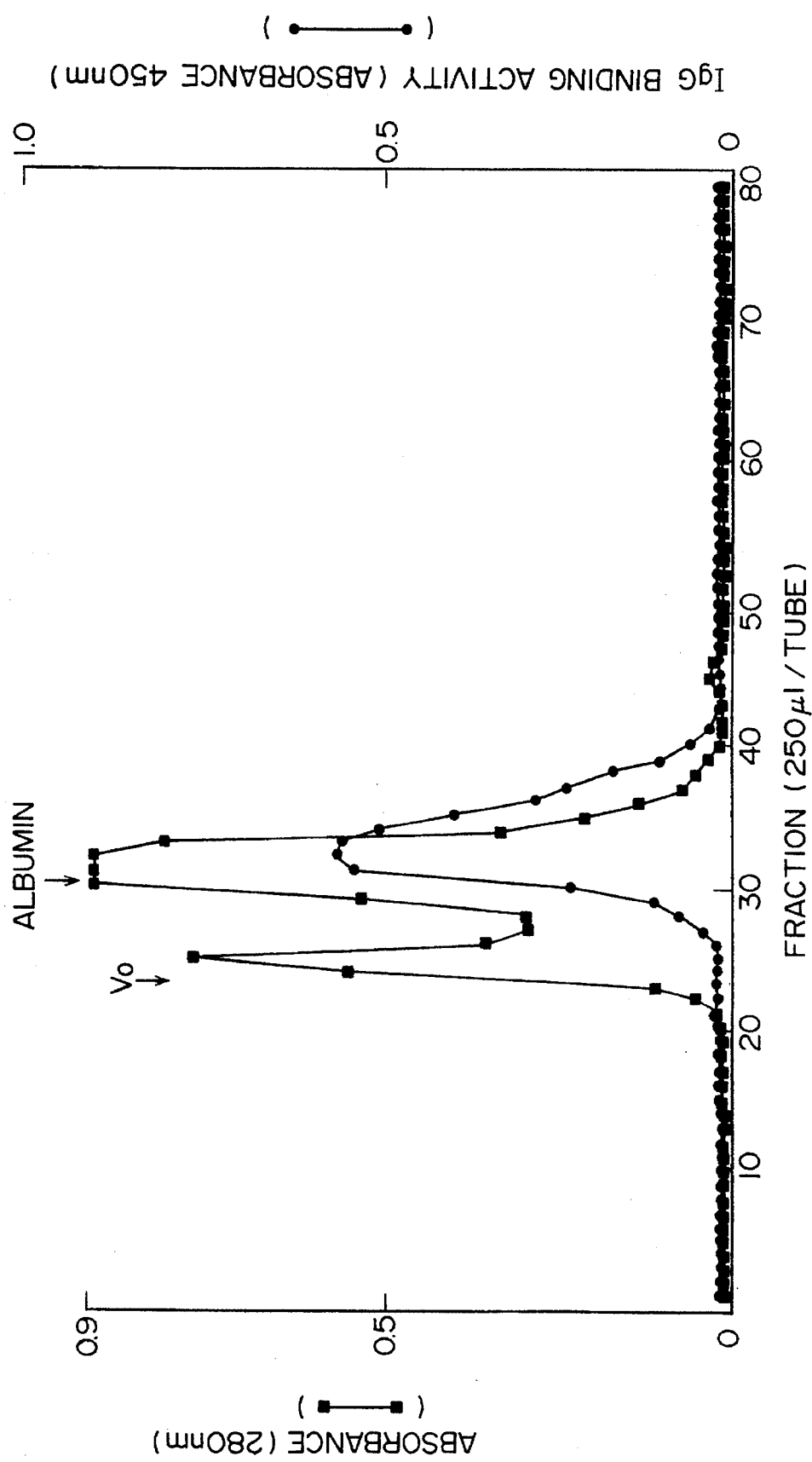

METHOD OF IMMUNOLOGICAL ASSAYING OF HUMAN OSTEOCALCIN, REAGENT AND KIT THEREFOR, ANTIBODY TO HUMAN OSTEOCALCIN, HYBRIDOMA PRODUCING SAID ANTIBODY, AND METHOD OF PRODUCING IT

This application is a continuation of now abandoned application, Ser. No. 08/038,544, filed Mar. 29, 1993, which was a continuation of abandoned application Ser. No. 07/582,849 filed Oct. 10, 1990.

FIELD OF THE INVENTION

This invention relates to a method of immunologically assaying human osteocalcin in a human assay sample, which permits diagnosis of the condition of metabolism of bones, a reagent therefor, an antibody to human osteocalcin, a hybridoma producing it, a method of producing it, and a series of techniques utilizing an antibody therefor. More specifically, this invention relates to a series of techniques by which a very trace amount of intact human osteocalcin or its fragment which can be contained in a human assay sample can be assayed distinguishably.

DESCRIPTION OF RELATED ART

Osteocalcin is a vitamin K-dependent bone calcium binding protein also called bone gla protein (BGP). Particularly, human osteocalcin is a relatively small protein composed of 49 amino acids and having a molecular weight of 5800.

This protein is produced from osteoblast, and occupies about 20% of the constituent components of non-collagen protein of the bones. This protein contains gamma-carboxyglutamic acid residues and has a strong affinity for hydroxyapatite, and it is therefore presumed to have an important role in the formation of the bone matrices.

Osteocalcin was first discovered from bones of chicken and bovine [(Proc. Nat. Acad. Sci., U.S.A., Vol. 72, No. 10, pp. 3925–3929 (October 1975), and ibid., Vol. 73, pp 1447–1451 (May 1975)]. Thereafter, the human osteocalcin was isolated, and its amino acid sequence was determined [The Journal of Biological Chemistry, Vol 255, No. 18, pp. 8685–8691, (1980)]. This literature shows the amino acid sequence of human osteocalcin in comparison with those of calf and swordfish, and shows that these osteocalcins have considerably similar structures.

On the other hand, the following reports were made on the assay of human osteocalcin.

(1) Proc. Natl. Acad. Sci., USA, Vol. 77, No.4, pp. 2234–2238 (1980)

P. A. Price et al. reported in this literature that assaying of human osteocalcin in a human plasma sample by radioimmunoassay by using a rabbit antibody to bovine, and stated that this rabbit antibody recognizes the C-terminal region of bovine osteocalcin.

(2) J. Clin. Invest., Vol. 66, pp. 878 883 (1980)

P. A. Price et al., in this publication, assayed human osteocalcin in a human plasma sample by radioimmunoassay by using a rabbit antibody to bovine osteocalcin as in the above literature, and recognized that a patient with a bone disease has an increased amount of osteocalcin as compared with a normal healthy person.

(3) J. Clin. Invest., Vol. 71, pp. 1316–1321 (1983)

P. D. Deimas in this literature examined the relation between the age of women and the amount of osteocalcin, and with showed age, the amount of osteocalcin increases. In this literature, it was described that human osteocalcin was assayed by the same method as P. A. Price et al. in (1) described above by using a rabbit antibody.

(4) Bone 6, 9–13 (1985)

B. D. Catherwood et al. examined the age of normal healthy persons and the amount of osteocalcin, and reported that with age, the amount of osteocalcin decreases little by little. According to the method of this literature, a peptide was synthesized which has an amino acid sequence of 37 to 49 on the C-terminal side of the human osteocalcin, prepared an antibody by using this peptide, and by utilizing the resulting antibody, assayed human osteocalcin by radioimmunoassay according to the competitive method.

(5) Japanese Laid-Open Patent Publications 209596/1988 and 160493/1989

These patent documents describe some monoclonal antibodies to bovine osteocalcin and their utilization, particularly they describe on a method of assaying human osteocalcin by the sandwich method by using a monoclonal antibody which recognizes C-terminal 45 (Phe)–49 (Val) and a monoclonal antibody which recognizes amino acids 21 (Gle)–30 (Asp) in the intermediate amino acid region. Acordingly, these methods also perform assaying a human blood sample by forming an assay system with an antibody to bovine osteoccalcin.

Problem Which the Present Invention Seeks to Solve

However, the above-stated prior assaying methods have some problems. The first problem in literatures (1) to (3) above is that because they use antibodies to parts common to bovine, these methods may possibly give erroneous results. As a basis for this, the osteocalcin content of human bones is very low as compared with the amount of osteocalcin in the bones of other animals, as it was proved by Poster et al. (J. B. C. 255, 8625 (1980)) using an immunoaffinity column. This suggests the possibility that human osteocalcin will differ from the osteocalcins of other animals in steric structure or physiological role.

Although the osteocalcin of an animal is similar to human osteocalcin in amino acid sequence, if antigens have different steric structures, an antibody obtained by the immunization of osteocalcin of an animal does not necessarily have a complete cross reactivity with human osteocalcin. Particularly, it would presumably be difficult to accurately detect the amount of osteocalcin existing in human serum. Hence, the prior methods do not accurately reflect the physiological significance of human osteocalcin.

The basis for the presumption that human osteocalcin differs in steric structure from bovine osteocalcin is also that the 17th amino acid residue of human osteocalcin from the N terminus is Glu, while that of bovine osteocalcin is Gla.

Gla is biosythesized from Glu by a transferase, gamma-carboxyglyutamic acid. This mechanism in osteocalcin is that this enzyme binds to the N-terminus side of a precursor protein of osteocalcin to convert Glu on the protein surface into Gla. Since only the 17th residues on the N-terminus of human is Glu different from that derived from an animal, it is presumed that different from the 17 Gla of other animal's osteocalcin, Glu exists at a configuration on which the action of Gla transferase does not extend. Accordingly, it is presumed that human osteocalcin has a different steric configuration from bovine osteocalcin.

The second problem of the prior assaying methods is in the sensitivity and reproducibility of the immunological assaying means. Since the amount of human osteocalcin in a human assay sample is extremely small. For example, since the concentration of osteocalcin in the serum of a normal healthy person is about 1 to 10 ng/ml, and that in a patient of a kidney disease or osteoporosis is about several tens of ng/ml. To measure such traces of osteocalcin accurately, it is necessary to establish an assaying system permitting a high level of sensitivity. However, the above-described Price et al. method and the Catherwood et al. method are so-called competitive methods using a radioactive substance. Accordingly, reproducibility and sensitivity become a problem because in the competitive method it is difficult to preset the conditions, and an assay system set up in accordance with the competitive method has poor reproducibility. As regards with specificity, one type of antibody is used. Hence, its specificity depends only upon one kind of antibody, and this method has low specificity in many cases.

As regards with sensitivity, one cannot deny that as compared with the sandwich method, the competitive method has a lower sensitivity.

In contrast, the assaying method described in (5) above in accordance with the sandwich method using a monoclonal antibody to bovine osteocalcin is superior to the prior methods. But this method still suffers from a great defect according to the sandwich method. This sandwich method uses a combination of a monoclonal antibody which recognizes the intermediate region of the amino acid sequence of osteocalcin and a monoclonal antibody which recognizes the C-terminus region of the amino acid sequence of osteocalcin. By this method, it is difficult to assay osteocalcin with high sensitivity. The reason for this is considered to be that since osteocalcin is a relatively small peptide composed of 49 amino acid residues, the epitopes of the above two antibodies are very near to each other.

The above-mentioned known assaying method further have another important problem in that by conventional assaying methods, an intact osteocalcin cannot be assayed distinguishably from its fragment. In view of the characteristics of the assay systems and the antibodies used in the conventional method, the conventional assaying methods assay intact osteocalcin and part of a fragment therof as a total without distinguishing them.

Recent studies have made it evident that to assay intact osteocalcin and a part of its fragment in an assay sample accurately in a distinguished manner becomes an important measure of judging the condition of the patient, the state of progress of the disease and the completion of therapy.

Osteocalcin is gamma-carboxylated by the action of vitamin K and participates in bone formation. It is reported that in bone absorption, most of osteocalcin may possibly dissolve in the form of some divided fragments [J. Clin. Invest. Vol. 77, pp. 1762–1767 (1986)]. Hence, an accurate measure of intact osteocalcin and its fragments in a human assay sample is useful to correctly judge whether the diseased condition of the patient tends to be bone absorption or bone formation.

The aforesaid conventional methods of assaying osteocalcins have the aforesaid defects in assay sensitivity. Furhtermore, they can not assay intact osteocalcin alone accurately, and they are not suitable for selectively assaying its fragments.

It is a first object of this invention to provide a a method of immunologically assaying intact osteocalcin in a human assay sample with high sensitivity, and a reagent and kit therefor.

A second object of this invention is to provide a method of immunologically assaying intact human osteocalcin and its fragments in a human assay sample together with high sensitivity, and a reagent and kit therefor.

Another object of this invention is to provide a method of assaying fragments of osteocalcin in a human assay sample with high sensitivity.

Still another object of this invention is to provide an immunological method for separating intact human osteocalcin with high sensitivity from a human assay sample or a sample containing intact human osteocalcin, and an immunoadsorbent body used in the method.

Yet another object of this invention is to provide a monoclonal antibodies and polyclonal antibodies which can be used for the above measuring methods, reagents, kits and the separating method, hybridomas producing these antibodies, and a process for producing these antibodies.

Further objects of this invention will become more apparent from the following description.

Means for Solving the Problem

Investigations of the present inventors have shown that the objects and advantages of this invention are partly achieved by (I) an assay system for intact human osteocalcin, (II) an assy system for the total amount of intact human osteocalcin and a fragment thereof, and (III) an assay system for the total amount of intact human osteocalcin and a fragment thereof.

Each of these assay systems will be described.

Assay System (1) of Intact Human Osteocalcin

According to this invention, there is provided a method of immunologically assaying human osteocalcin in a human assay sample using a solid phase antibody and a labelled antibody, wherein (1) one of the antibodies is an antibody to human osteocalcin having a specific epitope in a region of an amino acid sequence 1 to 20 on the N-terminal side of human osteocalcin or a fragment thereof having the same epitope as said antibody (inclusively referred to as the N-terminal antibody) and (2) the other antibody is an antibody to human osteocalcin having a specific epitope in a region of an amino acid sequence 36 to 49 on the C-terminal side of human osteocalcin, or a fragment thereof having the same epitope as said antibody (inclusively referred to as the C-terminal antibody).

There are also provided a reagent and a kit therefor.

According to this assay system (1), intact human osteocalcin in the assay sample can be selectively assayed with high sensitivity and a fragment of human osteocalcin cannot be assayed.

The assay system (1) of this invention is characterized in that two kinds of antibodies which recognize the N-terminal region and the C-terminal region in the 49 amino acid sequence of human osteocalcin are used in combination, and particularly the amino acid sequence of each terminal region is determined.

Specifically, one of the antibodies has a specific epitope in an amino acid sequence region from the N-terminal side (Tyr) to the 20th amino acid (Arg) of human osteocalcin, and the other antibody has a specific epitope in a region of the amino acid sequence from the C-terminus 36 (Ile) to 49 (Val) of human osteocalcin. In the assay system (1) of the present invention, the antibody which specifically recognizes the amino acid sequence region on the N-terminus side (N-terminus antibody) may be any of monoclonal antibodies and polyclonal antibodies to human osteocalcin, or a fragment thereof.

In the present invention, the fragment of the antibody has an equivalent epitope to the antibody and has an affinity for antigen. Specifically, it means a Fab', F(ab')$_2$ or Facb fregment, preferably Fab' or F(ab')$_2$ fragment.

On the other hand, the antibody which specifically recognizes a region of the amino acid sequence on the C-terminal side (C-terminus antibody) in the assay system (1) may be monoclonal antibodies and polyclonal antibodies to human osteocalcin, preferably the polyclonal antibodies. These antibodies may be fragments. Particularly, the C-terminal antibodies may be antibodies having an epitope in a region of an amino acid sequence from 40 (Glu) to 49 (Val) on the C-terminus side, or fragments thereof.

In the assay system (1), the N-terminal antibodies and the C-terminal antibodies give favorable results if they are polyclonal antibodies or fragments thereof. The labelled antibodies are advantageously Fab' and F(ab')$_2$ fragment. Desirably, labelled antibodies desiredly are labelled with enzymes.

In the assay system (I), a combination of a polyclonal antibody to human osteocalcin which antibody has a specific epitope in a region of an amino acid sequence 1 to 20 on the N-terminal side of human osteocalcin as a solid phase antibody, and a polyclonal antibody to human osteocalcin having a specific epitope in a region of an amino acid sequence 36 to 49 on the C-terminal side of human osteocalcin or an F(ab')$_2$ fragment thereof as the labelled antibody gives the best assaying sensitivity.

The monoclonal antibodies and polyclonal antibodies used in this assaying system (1), the preparation of these antibodies, and reagents and kits therefor will be described in detail hereinafter.

Assaying System (II) for the Total Amount of Intact Human Osteocalcin and its Fragment Furthermore, according to this invention there is provided a method of immunologically assaying the total amount of intact human osteocalcin and its fragment by using a solid phase antibody and a labelled antibody, wherein (1) one of the antibodies is a monoclonal antibody to human osteocalcin having a specific epitope in a region of an amino acid sequence 1 to 20 on the N-terminal side of human osteocalcin or a fragment of said monoclonal antibody having the same epitope as said antibody, and (2) the other antibody is a polyclonal antibody to human osteocalcin having a specific epitope in a region of an amino acid sequence 1 to 20 on the N-terminal side of human osteocalcin or a fragment of said polyclonal antibody having the same epitope. There are also provided a reagent and a kit therefor.

According to the assaying system (II), the total amount of intact human osteocalcin and a fragment therefor in an assay sample can be assayed with high sensitivity. The total amount of intact human osteocalcin and its fragment in the assay sample is a factor which by itself judges the diseased condition of the patient. If the assay system (II) is combined with the assay system (I), the difference in the assayed value between the two shows the amount the fragment of human osteocalcin in the assay sample, and the assay system (II) is significant in this sense. The amount of the fragment is a factor by which the condition of bone absorption can be accurately grasped. Heretofore, no assaying system has been know by which the fragment can be assayed selectively by distinguishing it from intact human osteocalcin.

The assaying system (II) of this invention is characterized in that a monoclonal antibody and a polyclonal antibody which recognize the N-terminal region of human osteocalcin are used in combination.

Specifically, one of the antibodies is a monoclonal antibody to human osteocalcin having a specific epitope in an amino acid sequence region of 1 (Tyr) to 20 (Arg) on the N-terminal side of human osteocalcin, or a fragment thereof, and the other is a polyclonal antibody having an epitope in an amino acid sequence region of 1 to 20 amino acids on the N-terminal side.

In this assaying system (II), the preferred combination is that of the monoclonal antibody or its fragment as the solid phase antibody, and the polyclonal antibody or its fragment as the labelled antibdy. Advantageously, the polyclonal antibody of the labelled antibody is a Fab' or F(ab')$_2$. The labelled antibody is desirably labelled with an enzyme.

Assay System (III) for Assaying the Total Amount of Intact Human Osteocalcin and its Fragment According to this invention, there is also provided a method of immunologically assaying human osteocalcin and its fragment in a human assay sample by using a solid-phase antibody and a labelled antibody, wherein the antibodies in the solid-phase antibody and the labelled antibody are polyclonal antibodies to human osteocalcin having a specific epitope in a region of an amino acid sequence 1 to 20 on the N-terminal side of human osteocalcin, or a fragment having the same epitope, the method being for the assaying of the total amount of intact human osteocalcin and its fragmemt. A reagent and a kit therefor are also provided.

According to the assay system (III), the total amount of intact human osteocalcin and its fragment is assayed with good sensitivity. In the assay sample (III), both the solid phase antibody and the labelled antibodies are polyclonal antibodies having an epitope in an amino acid sequence from 1 (Tyr) to 20 (Arg) on the N-terminal side of human osteocalcin or fragment thereof. In this assaying system (III), the labelled antibodies are preferably an F(ab') or (F(ab')$_2$ fragment of the polyclonal antibody. More preferably, the labelled antibodies are labelled with enzymes.

Preferred Embodiments of the Assaying Systems (I) to (III)

In the assaying systems (I) to (III), the combination of the solid-phase antibody and the labelled antibody and the effect and characteristics of the combination are as stated herein above. Now, specific means and preferred embodiments will be described in detail with respect to the method of assaying intact human osteocalcin and/or its fragment, and reagents and kits therefor. The following explanation has to do with means and embodiments common to the assaying systems (I) to (III) unless otherwise indicated.

(i) Human assay samples.

The human assay samples to be applied to the assay of this invention may be any human body fluid containing human osteocalcin or its fragment. Generally, it is preferably serum, plasma, urine of its equivalent, above all the serum.

(ii) Assaying means

In each of the assaying systems, a well known immunologicaal assaying method (so-called sandwich method) is used, and this method may be a one step method or two-step method.

One embodiment will be described below.

One of the antibody (primary antibody) is fixed to a suitable insoluble carrier (such as a plastic carrier (this antibody will be referred to as a fixed antibody). Then to avoid non-specific binding between the insoluble carrier and the reagent or assay sample to be measured, the surface of the insoluble carrier is coated with a suitable substance (such as bovine serum albumin). The insoluble carrier to which the first antibody is fixed is reacted with the assay sample at a fixed temperature for a fixed period of time, and during this time, the liquid phase antibody (first antibody) binds to the human osteocalcin and its fragment in the assay sample. The solid-phase antibody is then washed with a suitable washing solution, and a solution (aqueous solution) of the other antibody (second antibody) to human osteocalcin labelled with a suitable labelling substance (for example, an enzyme) is contacted with the second antibody at a fixed temperature for a fixed period of time to react with the second antibody. This is washed with a suitable washing solution. Then, the amount of the labelling substance labelled on the solid phased antibody on the insoluble carrier and existing on the second antibody through binding to the human osteocalcin and its fragment is measured.

The reaction in the above two-step method may be carried out by reacting the solid-phase antibody, the labelled antibody and the assaying sample containing human osteocalcin simultaneously and reacting them at a fixed temperature for a fixed period of time (1-step method).

Thus, from the above amount of the labelling substance, the total amount of human osteocalcin or the total amount of it and the fragment thereof can be calculated.

(iii) Assay reagent and kit

The assay reagent and kit in this invention is basically composed of a solid phase antibody and a labelled antibody as used in the assay systems (I) to (III) the combination of the respective antibodies and fragments thereof combined.

Specifically, the reagent for immunological assay of the total amount of intact human osteocalcin or its fragment is composed of one of the antibody or its fragment fixed to an insoluble carrier and the other being the other antibody or its fragments being labelled.

On the other hand, the kit for immunological assaying of the total amount of intact human osteoocalcin or its fragment is composed of (a) a solid-phase antibody, (b) a labelled antibody, (c) a dissolving agent, (d) a washing agent, and (e) where an antibody labelled with an enzyme is used, a substrate for measuring the enzyme activity, and a reaction stopper, the solid phase antibody (a) and the labelled antibody (b) being from the assay system (I) to (III).

Examples of the insoluble carrier used for the solid-phase antibody in the immunological assaying method, reagent and kit of this invention include polymers such as polystyrene, polyethylene, polypropylene, polyester, polyacrylonitrile, fluorine resins, cross-linked dextran and polysaccharide paper, glass, metal, agarose and combinations of these materials.

The shape of the insoluble carrier may be various for example, it may be in the form of a tray, a sphere, a fiber, a rod, a disk, a container, a cell or a test tube.

It is advantageous to use an enzyme, a fluorescent substance, a light-emitting substance. The enzyme may be, for example, peroxidase, alkaline phosphatase, and beta-D-galactosidase, Examples of the fluorescent substance are fluorescein isocyanate and phycobiliprotein. Examples of the light-emitting substance are isoluminol and lucigenine. Examples of the radioactive substances include $^{125}I$, $^{131}I$, $^{14}C$ and $^{3}H$. The examples are not limited to these illustrated, and any other materials that can be used in immunological assays may be used.

When the labelling substance is an enzyme, a substrate for measuring its activity and as required, a color forming agent may be used. When peroxidase is used as the enzyme, it is possible to use $H_2O_2$ as a substrate and 2,2"-azinodi-[3-ethylbenzothiazolinesulfonic acid] ammonoiuiuim salt (ABTS), 5-aminosalicylic acid-phenylenediamine, 4-aminoantipyridine, and 3,3',5,5'-tetramethylbenzidine may be used as color-forming agents. When alkaline phosphatase is used as the enzyme, o-nitrophenyl phosphate may be used as the substrate. When beta-D-galactosidase is used as the enzyme, fluorescein -di-(beta-D-galactopyranoside), 3-methylumberiferyl, etc. may be used as substrates.

In the kit for immunological assay in this invention, the dissolving agent (c) may be any of those which are well used for immunological assay, and preferred examples are a phosphase buffer, a Tris-HCl buffer and an acetate buffer having a pH in the range of 6.0 to 8.0. The washing agent (d) may be those which are generally used for immunological assay, and specific examples include physiological saline, a phosphate buffer, a Tris-HCl buffer and a mixture of these. The, washing agent may further contain a nonionic surface-active agent such as triton X-100, Tween 20 or Brig 35 and an ionic surface-active agent such as sodium dodecylsulfate.

(iv) Use of an insoluble carrier having a smooth surface

Investigations of the present inventors have shown that the use of an insoluble carrier having a smooth mirror-surface finish in the system of assaying human osteocalcin or its fragment permits increased measuring sensitivity and increased stability while nonspecific adsorption of a protein in an assay sample or a labelled antibody to the carrier is inhibited as compared with a carrier having a coarse surface. In the past, to increase the assay sensitivity in the immunological assaying system, an insoluble carrier having its surface roughened by polishing to increase its surface area was used. But in the case of human osteocalcin or its fragment which is contained only in a trace amount in an assay sample, as the smoothness of the surface increases, non-specifc adsorption is inhibited, and the assaying sensitivity increases.

Thus, the insoluble carrier is advantageously has a smooth surface of mirror-surface finish having a surface centerline roughness (Ra) of not more than 1.5 micrometers.

The centerline average roughness (Ra) means the following formular Ra expressed in microns $$Ra = \frac{1}{l} \int^{l} o/f(x)/dx$$

in which the portion having the measured length of l is extracted in the direction of its centerline from the roughness curve, the centerline of the extracted portion is made X axis, and the direction of the longitudinal multiplication is made Y axis. The roughness curve is expressed as y=f(x).

JIS B0601-1982 (Japan), ANSI B46.1-1979 (USA) and R 468-1966 (ISO) explain the centerline average roughness (Ra).

In the following Examples of the present invention, the surface roughness of the insoluble carrier was measured by using a surface roughness tester SURFCOM®.

There is no particular restriction on the material and shape of the insoluble carrier having the aforesaid smooth surface, and they may be those which are explained in the foregoing. An especially preferred example is a polystyrene bead.

(v) Addition of a specific protein in an immunological reaction

It has been found that when a protein having a molecular weight of 16,000 to 50,000 and an isoelectric point of 1.0 to 5.0 or a mixture containing it is present in an immunological reaction solution in an immunological assay system of this invention and the final concentration of it in the immunological reaction solution becomes 0.02 to 0.9% by weight, non specific adsorption is inhibited, and therefore, the background becomes low and high sensitivity becomes easy to obtain preferably. The protein or the mixture containing it can be included in the immunological assaying reagent so that it becomes in the predetermined amount in the immunological reaction solution in the immunological assaying reagent constituting part of the reagent and kit used in the immunological assaying method of this invention. Examples of such proteins include, for example, casein, pepsin, ovoglycoprotein and orosomucoid. Such a mixture may contain 10 to 60% by weight, preferably 20 to 50% by weight, of proteins, 30 to 80% by weight, preferably 40 to 60% by weight, of sugars (such as lactose), fats (for example 0.5 to 2% by weight), and ashes (for example, 5 to 12% by weight), and water (for example 2 to 9% by weight) as main components. A typical example of such a mixture is skim milk. Skim milk contains casein as a protein. As compared with the use of casein alone, the skim milk has good dispersibility in the immunological reaction solution, has a higher effect of reducing non-specific adsorption, and has good preservability at 4° C. (difficulty of forming a precipitate). The skim milk may be any defatted milk of any origin. A typical example is the skim milk made by Difco Co., Ltd. which is on the market.

Method of Assaying Human Osteocalcin Fragment

As stated above, according to the assaying system (I) of this invention, intact osteocalcin in a human assay sample can be assayed with high sensitivity by distinguishing it from its fragment. On the other hand, according to the assaying system (II) or (III), the total amount of intact human osteocalcin and its fragment in a human assay sample can be measured with high sensitivity. Accordingly, from the results with these measuring systems, the amount of the fragment of human osteocalcin in the human assay sample can be exactly known. Heretofore, no method was known for correctly measuring the amount of the fragment of human osteocalcin by distinguishing it from intact human osteocalcin.

Thus, according to this invention, there is provided a method of assaying human osteocalcin fragment which comprises (i) measuring the total amount of intact human osteocalcin and its fragment in an assay sample in accordance with the measuring methods in the assay system (II) or (III), (ii) measuring intact human osteocalcin in a human assay sample in accordance with the measuring method in the assay system (I), and (iii) then calculating the difference betweeen the value measured in (i) and the value measured in (ii).

By such assaying method, the amount of the fragment of human osteocalcin in a human assay sample accurately by distinguishing it from intact humam osteocalcin. The amount of the fragment of human osteocalcin is considered as one measure for knowing the state of bone absorption, and measurement of its amount is useful for judgement of various diseased conditions.

Methods of Separating and Purifying Intact Human Osteocalcin

By using the above-mentioned N-terminal antibody, intact human osteocalcin can be easily separated from a liquid containing intact human osteocalcin. Furthermore, intact human osteocalcin purified to a high degree can also be obtained from that liquid. Thus, there are provided a method of separating and a method of purifying intact human osteocalcin according to the following methods (1) and (2).

Method 1

A method of separating intact human osteocalcin, which comprises (i) contacting a liquid containing intact human osteocalcin with a solid phase to which is fixed an antibody to human osteocalcin having an epitope in a region of an amino acid sequence having 1 to 20 amino acids on the N-terminal side of human osteocalcin or a fragment (N-terminal antibody) having the same epitope, to adsorb intact human osteocalcin to the solid phase, (ii) then contacting an eluent with the solid phase to which intact human osteocalcin is absorbed to elute intact human osteocalcin from the solid phase, and (iii) separating intact human osteocalcin from the resulting eluting liquid containing intact human osteocalcin.

Method 2

Steps

A method of separating intact human osteocalcin from a liquid containing intact human osteocalcin, which comprises (a) contacting a liquid containing intact human osteocalcin with a first solid phase to which an antibody to human osteocalcin is bound to adsorb intact human osteocalcin to the first solid phase, (b) contacting an eluting solution with the first solid phase on which intact human osteocalcin is adsorbed to elute the intact human osteocalcin from the first solid phase, (c) contacting the resulting eluting solution containing intact human osteocalcin with a second solid phase to which another antibody to human osteocalcin is bound to adsorb intact human osteocalcin on the second solid phase, (d) contacting an eluting solution with the second solid phase on which intact human osteocalcin is adsorbed to elute intact human osteocalcin from the second solid phase, and (e) separating the purified intact human osteocalcin from the resulting eluting solution containing intact humam osteocacin;

(f) wherein the antibody bound to one solid phase is an antibody to human osteocalcin having a specific epitope in a region of an amino acid sequence 1 to 20 on the N-terminal side, or a fragment thereof (N-terminal antibody) having the same epitope, and (g) the antibody bound to the other solid phase is an antibody to human osteocalcin having a specific epitope in the amino acid sequence region 36 to 49 on the C-terminal side of human osteocalcin, or a fragment thereof (C-terminal antibody) having the same epitope.

According to the methods 1 and 2, intact human osteocalcin can be separated with good purity from a liquid containing intact human osteocalcin. In particular, according to the method 2, intact human osteocalcin having a very high purity can be separated. The resulting intact human osteocalcin can be used as a reagent, an authentic sample or a drug component.

In the methods 1 and 2, the liquid containing intact human osteocalcin may contain intact human osteocalcin. Its concentration may be irrelevant, and various. For example, it may be a human body fluid or its treated product (such as serum, plasma or urine). Or it may be a liquid containing intact human osteocalcin artificially produced by gene manipulation.

The N-terminal antibody and the C-terminal antibody used in methods 1 and 2 may be explained hereinabove with regard to the assay systems (I), (II) and (III). These antibodies are desirably polyclonal antibodies or fragments thereof. The insoluble carriers described with regard to the assay systems (I), (II) and (III) may be directly used as the solid phase to which the antibodies are to be bound. Of these solid phases, a dextran gel, an agarose gel and a polyvinyl gel are preferred.

In the methods 1 and 2, the eluting solutions used to elute intact human osteocalcin adsorbed on the solid phase may be any of usually known acidic buffers.

Immunoadsorbents

By using the antibodies discovered by the present inventors to human osteocalcin and binding them to a solid phase, the following three types of immunoadsorbents are provided.

(i) An immunoadsorbent comprising a monoclonal antibody to human osteocalcin having a specific epitope in a region of an amino acid sequence from 1 to 20 on the N-terminal side of human osteocalcin, or a fragment thereof having the same epitope which is bound to a solid phase.

(ii) An immunoadsorbent comprising a polyclonal antibody to human osteocalcin having a specific epitope in a region of an amino acid sequence from 1 to 20 on the N-termianl side of human osteocalcin, or a fragment thereof having the same epitope which is bound to a solid phase.

(iii) An immunoadsorbent comprising a polyclonal antibody to human osteocalcin having a specifc epitope in an amino acid sequence 36 to 49 on the C-terminal side of human osteocalcin or a fragment thereof having the same epitope which is bound to a solid phase.

Since the immunoadsorbents can adsorb intact human osteocalcin thereon, they can be used as adsorbents in the above-mentioned method of separating intact human osteocalcin from the solid phase in the above immunoadsorbents may be the insoluble carriers described in the assay systems (1), (II) and (III), specifically, they are preferably a dextran gel, an agarose gel, a polyvinyl gel or metal particles. The antibody may be bound to the insoluble carrier by an ordinary method, for example, by the bromocyan method, or via epoxy, amino, carboxyl, or formyl group.

Monoclonal Antibodies

According to this invention, there is provided a monoclonal antibody to human osteocalcin having a specific epitope in a region of an amino acid sequence 1 to 20 on the N-terminal side of human osteocalcin.

The monoclonal antibody of this invention can be prepared by cultivating hybridoma cells prepared by the cell fusion method (G. Koehler and Milstein, Nature (London), 256, 495–497 (1975), and separating them from the culture liquid. Specifically, a peptide (to be abbreviated as $^1$Try-$^{20}$Arg) having the following N-terminal sequence of human osteocalcin, $^1$Try-Leu-Tyr-Gln-Trp-Lue-Gly-Ala-Pro-Val-Pro-Tyr-Pro-Asp-Pro-Leu-Glu-Pro-Arg-$^{20}$Arg, was synthesized, and a carrier protein was bound to it. Mice were immunized with the resulting protein fragment. Lymphocytes of the mice were then fused with mouse myeloma cells to prepare hybridoma cells. Since the hybridomas obtained produce various monoclonal antibodies according to the fused lymphocytes, the hybridomas producing the desired monoclonal antibody were isolated as cloned hybridomas. The cloned hybridomas were cultivated in vitro to secrete monoclonal antibodies. From the cultivation supernatant, the monoclonal antibodies to the N-terminal amino acid sequence of human osteocalcin were isolated.

Now, the the specific method of preparing the monoclonal antibodies to the N-terminal amino acid sequence of human osteocalcin of the invention will be described in details.

A. Preparation of an antigen

As an antigen, there may be used human osteocalcin, a peptide having the amino acid sequence of human osteocalcin obtained by enzymatically cleaving human osteocalcin, or a synthetic peptide. Here, the case of using a synthetic peptide ($^1$Try-$^{20}$Arg) will be described.

1) The peptide shown in FIG. 1 was synthesized by inserting cystein in the 20th and 21st residues of the N-terminal amino acid sequence of synthetic human osteocalcin in the N-terminal peptide ($^1$Try-$^{20}$Arg).

For the synthesis, a peptide synthesizer of ABI company was used. The resulting peptide is called Ost-N(20).

2) Preparation of an antigen (a product obtained by binding Ost-N(20) to a carrier protein).

Keyhole limpet hemocyhanine (KLH), a typical carrier protein, was used as a carrier protein, and treated with N-(m-maleimidebenzoic acid(-N-succinimide ester (MBS). On the other hand, Ost-N (20) was treated with 2-mercaptoethanol to make the SH group free, and while adding dropwise Ost-N (20) to MBS-treated KLH, the reaction was carried out while the reaction solution was maintained at a pH of 6.0 to 6.5. After reaction for 3 hours, the reaction solution was dialyzed, and the resulting product was used as an antigen.

B. Preparation of antigen-stimulated lymphocytes by means of synthetic peptide-KLH bonded product Male Balb/c mice were used. But mice of other strains, rats, rabits and guinea pigs, from which antigen-stimulated lymphocytes can be taken may be used without restriction. There may also be used a method by which lymphocytes of an animal or a human lymphocytes are taken, and antigen-stimulated lymphocytes can be obtained in vitro.

The synthetic peptide-KLH bound product was intraperitoneally administered in an amount of 10 to 100 micrograms together with a complete Freund's adjuvant, and thereafter, at an interval of 3 to 4 weeks, the same amount of the KLH bound product was intraperitoneally administered together with an incomplete Freund's adjuvant. During this period on the 10th day after each administration, the blood was drawn to measure the serum antibody titer, and it was confirmed that the antibody titer increased to more than 50000 times. 1 to 50 micrograms of synthetic peptide-KLH bound product was intravenously administered, and 3 to 4 days later, the spleen was aseptically taken out, and a suspension of the spleen cells was prepared. As the antigen-stimulated lymphocytes, the spleen cells are well used, but they may be lymphonode cells and lymphocytes of the peripheral blood.

C. Cell fusion

The antigen-stimulated spleen cells were fused with mouse myeloma cells in the presence of a fusion promoter by a method generally used (for example, Lectures in Experimental Biochemistry, Continued, Vol. 5, pages 70–71, Tokyo Kagaku Dojin).

Other method by which the desired cell fusion is possible may also be used, for example, an electrical fusing method may be used.

As the mouse myeloma cells, many lines suitable for cell fusion are known, and any of these lines may be used. In the present invention, P3-X63-Ag8-U1 cells (abbreviated as P3U1) [D. E. Yelton et al., Current Topics in Microbiology and Immunology, 81, 1 (1978)] was used.

As a fusion promoter, polyethylene glycol having an average molecular weight of 1,000 to 5,000 may be used. Other fusion promoters known in the art may also be used.

D. Obtaining a cloned hybridoma

A cell suspension subjected to cell fusion, i.e. a mixture of unfused spleen cells and myeloma cells and fused cell (hybridoma) is diluted with a selective medium in which only the hybridoma can survive. The diluted cell suspension was added to another vessel (microtiter plate), and cultivated for a time sufficient to cause the unfused cells to die (about 1 hour).

The medium used was drug-resistant (for example, 8-azaguanine-resistant) and does not grow the unfused myeloma cells (for example, hypoxanthine, aminopurine and thymidine (HAT) medium.

After the hybridoma grew in the cultivation vessel, its cultivation supernatnat is taken, and for a monoclonal antibody to synthetic peptide Ost-N(20), the supernantant was screened by the enzyme linked immunosorbent assay (ELISA for short).

The resulting hybridoma obtained in a vessel which was antibody-positive was cloned by a generally used method (such as a limiting dilution method, a soft agar method, or a cloning by using a fibrin) to obtain cloned hybridoma which secreted anti-human osteocalcin monoclonanl antibodies.

E. Preparation of an anti-human osteocalcin monoclonal antibody from the culture liquid of hybridoma Cloned hybridomas were cultivated and grown peritoneally in mouse, and the ascites or serum thereof was taken. From it, anti-human osteocalcin monoclonal antibodies were separated by methods well known generally (for example, precipitation with ammonium sulfate, DEAE-cellulose column, protein-Aaffinity column).

The cultivation of the hybridoma may also be carried out intraperitoneally in nude mice or nude rats, or by using a suitable nutrient medium in vitro.

The monoclonal antibodies in accordance with this invention have a specific epitope in a region of an amino acid sequence 1 to 20 on the N-terminal side of human osteocalcin. Furthermore, this monoclonal antibody of the invention also binds to a peptide having an amino acid sequence 1 to 19 on the N-terminal side of human osteocalcin. This monoclonal antibody has cross reactivity of not more than 50% with bovine osteocalcin.

This monoclonal antibody is used in an imunoadsorbent in the assay systems (I), (II), and (III) in accordance with this invention and the separating method of this invention.

Polyclonal Antibody (I)

According to this invention, there is provided a polyclonal antibody to human osteocalcin having a specific epitope in a region of an amino acid sequence 1 to 20 on the N-terminal side of human osteocalcin. This polyclonal antibody has a cross reactivity of not more than 50% with respect to bovine polyclonal antibody. This polyclonal antibody also binds to a peptide having an amino acid sequence 1 to 19 in the N-terminal side of human osteocalcin.

This polylocnal antibody may be obtained from an animal which is immunized with a polypeptide obtained by binding a carrier protein to a peptide represented by the following amino acid sequence:

H-Try-Leu-Tyr-Gln-Trp-Leu-Gly-Ala-Pro-Val-Pro-Tyr-Pro-Asp-Pro-Leu-Glu-Pro-Arg-Arg-OH.

A method for immunization is that the peptide is converted into relatively large molecules and mixed with adjuvant, and the mixture is administered to an animal to be immunized to prepare an antibody in accordance with a method known per se.

In immunization, to convert the peptide into larger molecules, there may be used a method of binding a carrier protein to the peptide and a method of binding the peptide to another high molecular substance. Examples of the carrier protein include albumin, keyhole limpet hemocyanine (KLH) and protein A. Of these, the albumin and KLH are preferred. Examples of other high molecular weight substances are water-soluble polymers such as polyvinylpyrrolidone.

In binding a carrier protein to the peptide, carbodiimide is used when the terminal COOH of the peptide is utilized. On the other hand, when the $NH_2$ terminal group is utilized, glutaraldehyde is preferably used. Where a more specific binding is to be sought, cystein is introduced into the peptide, and into the carrier protein, a maleimide group or dithiopyridyl group is introduced or a dithiopyridyl group is introduced, and these groups are bound to each other.

As the adjuvants, a complete Freund's adjuvant and an incomplete Freund'd adjuvant or aluminum hydroxide are used.

Examples of animals to be immunized include sheep, rabbits, horses, dogs, mice, guinea pigs, and swine.

Polyclonal Antibody (II)

Furthermore, according to this invention, there is provided a polyclonal antibody to human osteocalcin having a specific epitope in a region of an amino acid sequence 43 (Arg) to 49 (Val) on the C-terminal side of human osteocalcin.

Such a polyclonal antibody can be obtained by immunizing an animal with a polypeptide obtained by binding a peptide having the following amino acid sequence:

H-Arg-Arg-Phe-Tyr-Gly-Pro-Val-OH to a carrier protein and taking out the resulting polyclonal antibody from the immunized animal.

The method for immunization may be basically the same as that described with regard to the polyclonal antibody (I).

BRIEF DESCRIPTION OF THE DRAWINGS

FIG. 1 shows the amino acid sequence of a synthetic peptide obtained by introducing cystein in 21st residue of human osteocalcin with 1 to 20 residues on the N-terminal side of human osteocalcin which was prepared in Example 1 (A).

FIG. 2 shows the amino acid sequence of a synthetic peptide having 43 to 49 residues on the C-terminal side of human osteocalcin prepared in Example 2 (A).

FIG. 3 shows the amino acid sequence of a synthetic peptide having cystein in the 35th residue in the 36 to 48 residues on the C-terminal side of human osteocalcin prepared in Referential Example (A).

FIG. 6 shows the results of measurement of the reactivity of intact human osteocalcin or its fragment in Example 4.

FIG. 7 shows the conditions for flowing of a buffer using the reverse phase HPLC in Example 5.

FIG. 11 shows the results of measurement of the total amount of intact human osteocalcin and its fragment in the assay system (III) in accordance with Example 8.

FIG. 12 shows the results of measurement of intact human osteocalcin in accordance with Example 12.

Example 13 shows the results of measurement of the total amount of intact human osteocalcin and its fragment, in the assay system (II) in accordance with Example 14.

Figure 14:
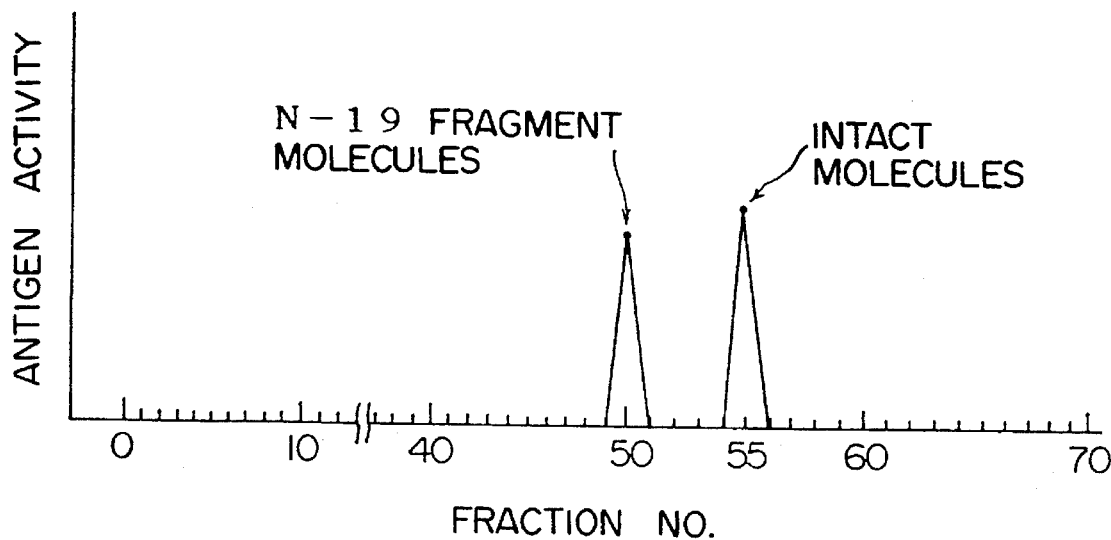

FIG. 14 shows the antigenic activity of each fraction of human osteocalcin in accordance with Example 16.

Figure 15:
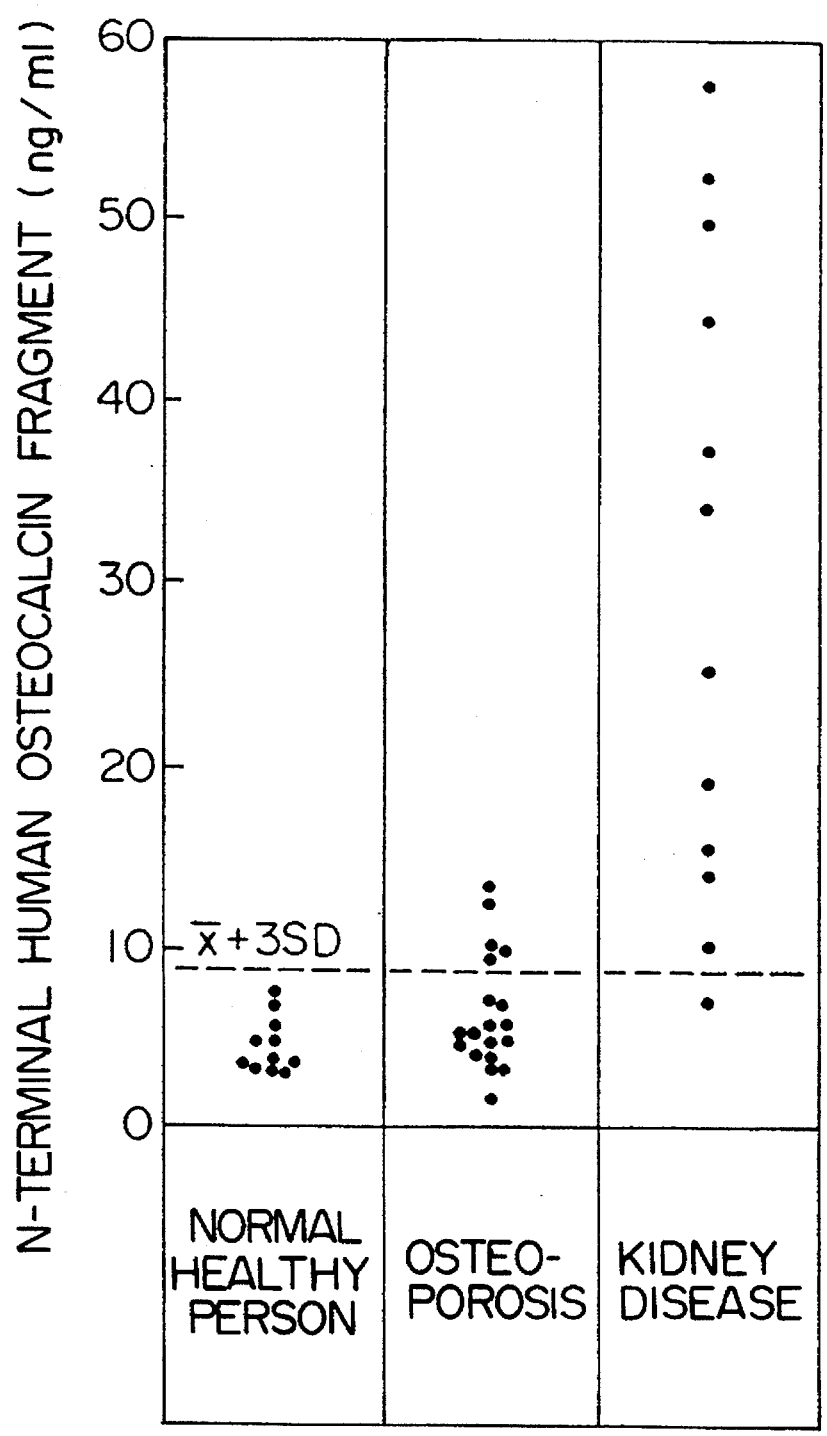

FIG. 15 shows the results of measurement of a N-terminal fragment of human osteocalcin in the sera of a healthy person, a kidney disease patient and an osteoporosis patient in Example 17.

Figure 16:
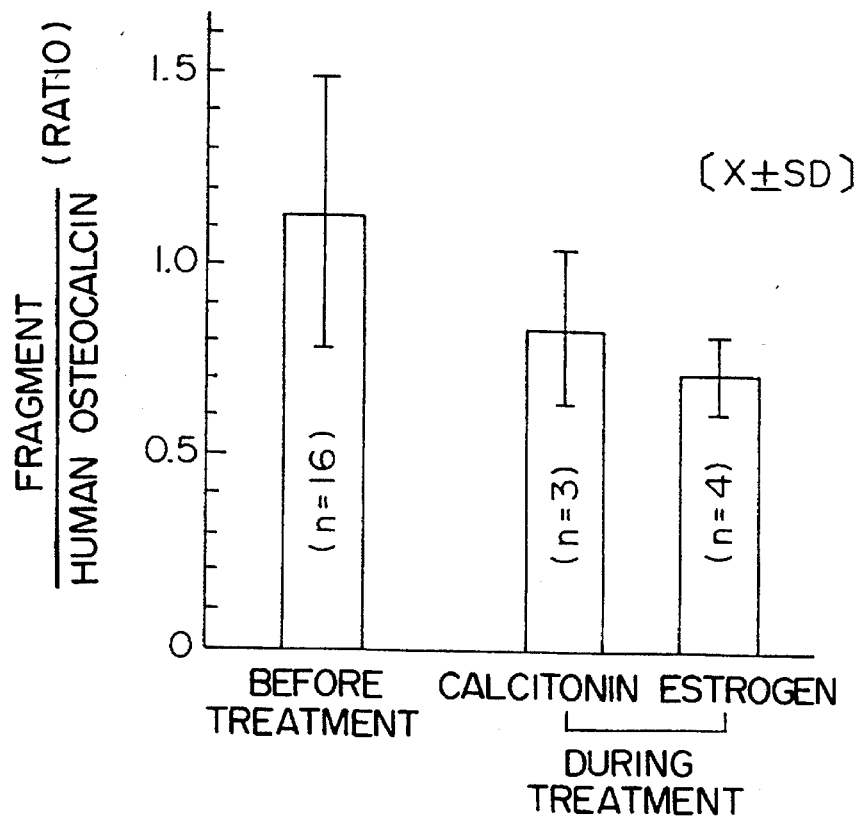

FIG. 16 shows the clinical significance in the measurement of human osteocalcin fragment in Example 18.

EXAMPLES

In the following, the present invention will be described in detail by Examples. They are given for an easy understanding of the present invention, and the present invention is in no way limited to these examples. All "%" are by "% by weight".

Example 1

Preparation of a Polyclonal Antibody Having an Epitope in a Region of an Amino Acid Sequence 1 to 20 on the N-terminal Side (A) Synthesis of a peptide having 1 to 20 residues Into the N-terminal of human osteocalcin, a specific amino acid sequence 1 to 20 residues and cystein was introduced into the 21st residue to synthesize the peptide shown in FIG. 1.

For the synthesis, a peptide synthesizer of the ABI company was used. The resulting peptide was named Ost-N (20).

(B) Preparation of antigen (OSt-N (20) to which a carrier protein is bound. Keyhole limpet hemocyanine (KLH) was used as a carrier protein, and treated with N-(m-maleimide-benzoic acid)-N-succimide ester (MBS). On the other hand, Ost-N (20) was treated with 2-mercaptoethanol to render the SH group free. While Ost-N(20) was added dropwise to MBS-treated KLH, the reaction solution was reacted while its pH was maintained at 6.0 to 6.5. After reaction for 3 hours, the reaction solution was dialyzed, and the resulting product was used as an antigen.

(C) Preparation of a polyclonal antibody

The KLH-bound product of Ost-N (20) was immunized in a rabbit in an amount of 500 micrograms/shot. After immunization 6 times at two weeks intervals, the antibody titer increased. The blood was thus drawn and the antibody was purified with Protein A-Sepharose to obtain the desired antibody.

Example 2

Preparation of a Polyclonal Antibody Having an Epitope in a Region of an Amino Acid Sequence 43 to 49 Positions on the C-Terminal (A) Synthesis of a peptide having amino acid redues 43 to 49 on the C-terminal A peptide shown in FIG. 2 having a specific amino acid sequence 43 to 49 amino acid residues on the C-terminal of human osteocalcin was synthesized by using the peptide synthesizer of ABI company. This peptide was named Ost-C(7).

(B) Preparation of an antigen (the bound product of a carrier protein to Ost-C(7)

Equal weights of Ost-C(7) and KLH were mixed and reacted with carbodiimide (DCC) to prepare a bound product of Ost-C(7) and KLH.

The resulting product was purified by gel filtration of HPLC.

(C) Preparation of a polyclonal antibody

The KLH-bound product of Ost-C (7) was immunized in rabbits in a dose of 500 micrograms/shot. Then by operating in the same way as in Example 1, the desired antibody was obtained.

Referential Example

Preparation of a Polyclonal Antibody Having an Epitope in a Region of an Amino Acid Sequence 35 to 49 Positions on the C-terminal Side (A) Synthesis of an amino acid residues 35 to 49 positions on the C-terminal A peptide shown in FIG. 3 was synthesized which contained specific amino acid sequence 36 to 49 residues on the C-terminal of human osteocalcin and having cystein at the 35th position.

For the synthesis, the peptide synthesizer of ABI Company was used. This peptide was named Ost-C(15)

(B) Binding of a carrier protein to Ost-C(15)

By using the same method as in Example 2, (B), KLH was bound to the Ost-C(15).

(C) Preparation of a polyclonal antibody

By using the same method as in Example 2, (C) and by using the KLH-bound product of Ost-C(15) an antigen, the desired antibody was obtained.

Example 3

Structure of Intact Human Osteocalcin Assaying System (I)

(A) Preparation of an antibody labelled with horse-radish peroxidase (HRP)

(1) Labelling of anti-Ost-N(20) antibody (IgG) with HRP 50 microliters of a dimethyl formamide solution of MBS in a concentration of 10 ml/ml was added to 2 ml of a solution of 0.01M phosphate and 0.15M NaCl (pH 7.4)

containing anti-Ost-N(20) antibody obtained in the previous Example in a concentration of 1 mg/ml, and they were reacted at 25° C. for 30 minutes. Then, by using column filled with Sephadex G-25, the reaction solution was gel-filtered with 0.1M phosphate buffer (0.1 MPB) (pH 5.0) to separate the unreacted MBS from the maleimidized antibody.

On the other hand, 120 microliters of a 60 mg/ml dimethylformamiode solution of acetylmercaptosuccinyl anhydride was added to 2 ml of a solution of 10 mg/ml of HRP in 0.1 MPB (pH 6.5), and they were reacted at 25° C. for 2 hours. Then, 600 microliters of 0.1M Tris-HCl buffer (pH 7.0), 160 microliters of 0.1M EDTA, and 1.5 ml of hydroxylamine were added, and the entire reaction solution was reacted at 0° C. for 4 minutes. Thereafter, the reaction solution was put in a collodion bag, and dialyzed at 4° C. for 3 days to obtain mercaptosuccinyl HRP.

Then, 2 ml of the maleimide acylated antibody was mixed with 4 mg of the mercaptosuccinyl HRP. The mixture was concentrated in a collodion bag under ice cooling until the protein concentration became 4 to 10 mg/ml. Then, the mixture was allowed to stand overnight at 15° to 20° C. The liquid was gel-filtered with a commn filled with ultrogel ACA 44 (LKB Company) to obtain HRP-labelled anti-Ost-N(20) antibody.

(2) Labelling of anti-Ost-N(20) antibody F(ab')$_2$ with HRP 100 microliters of a 1M acetate buffer (pH 4.2) and and a solution of 20 microliters of pepsin in 20 microliiters of the same buffer were added to 1 ml of 2.0 mg/ml of anti-Ost-N(30) antibody PBS solution obtained in Example, and the mixture was reacted at 37° C. for 4 hours. After the reaction, the reaction solution was separated by using a Sephadex G25 column (2 cm×45 cm) equilibrated with PBS, and the isolated F(ab')$_2$ was collected. As in Example 1 (A) (1), anti-Ost-N(20) F(ab')$_2$ antibody labelled with HRP was prepared.

(3) Labelling of anti-Ost-N(20) antibody (Fab') with HRP

An F(ab')$_2$ fraction of anti-Ost-N(20) antibody was prepared in accordance with (2) by using mercaptoethylamine to reduce it, and by gel filtration HPLC on a Toso G3000 SW column, Fab' was purified.

On the other hand, in accordance with maleimidization of anti-Ost-N(20) antibody in Example 3 (A) (1). Then, the anti-Ost-N(20)antibody (Fab'), 2 mg, and 4 mg of the maleimidized HRP were mixed and the mixture was concentrated by a philtron (ultrafiltration device), and reacted at 4° C. for 16 hours. The product was isolated and purified by gel filtration HPLC on a Toso G 3000 SW column to obtain HRP-labelled anti-Ost-N(20)(Tab') antibody (B) Preparation of an antibody-fixed beads (1) Fixation of an antibody Polystyrene beads (diameter 6 mm) were well washed and then left to stand for one day at 4° C. in a PBS solution of each of anti-Ost-C (7) and anti-Ost-C(15 antibody, and then washed with PBS. In a PBS solution of a 1% bovine serum alubumin (BSA), each of the antibodies was left to stand for a day and a night at 4° C. and post-coated to obtain beads to which the anti-Ost-C-(7) and anti-Ost-C(15) antibody were fixed.

(2) Evaluation of the activity of antibody-fixed beads.

The activity of each of the anti-Ost-C (7) and anti-OSt-C (15antibody prepared in (1) above was examined by the following technique. Each of the beads to which each antibody was fixed, and 0.05M Tris-HCl containing 1% BSA and 0 to 50 ng/ml of purified human osteocalcin (standard substance), 200 microliters of 0.15M NaCl buffer (0.05M TBS) (pH 8.0), and 200 microliters of 0.05M TBS (PH 8.0) solution containing 1% BSA and a Fab' fraction of HRP-labelled anti-Ost-N(20) were added to a test tube, and they were incubated at 4° C. for 17 hours. Then the solution in the test tubre was removed by suction, and after the test tube was washed with 0.05M TBS (pH 8.0). Then, a 0.1M phosphase/citrate buffer (pH 4.3) containing 2.5 mM 3,3',5,5'tetramethylbenzidine hydrochloride was added in an amount of 0.4 ml to each test tube. Then, the reaction was carried out at 25° C. for 30 minutes. One milliliter of a 1N aqueous solution of sulfuric acid was added to stop the enzyme reaction.

Then, this solution was examined by a spectral photometer to measure the absorption intensity at a wavelength of 450 nm, and plotted against 0 to 100 nm/gl of the concentration of the standard substance. The results are shown in Table 4.

(C) Structure of the assay system

One bead to which anti-Ost-C (7) was fixed, as prepared in Example 3, (B), (1) 200 microliters of 0.05M TBS (pH 8.0) containing 1% BSA and 0 to 320 ng/ml of purified human osteocalcin (standard substance) 200 microliters of 1% BSA-containing 0.05M TBS (pH 8.0) solution of each of the HRP-labelled antibodies prepared in Example 3 (A), (1) to (3) were added to each test tube by combining the antibody-fixed beads with IgG and F(ab')$_2$ fragment of HRP-labelled antibody, and incubated at 25° C. for 2 hours. Then, the solution in the test tube was removed by suction. The test tube was washed with 0.05M TBS (pH 8.0), and then 0.1M phosphate buffer (pH 4.3) containing 3,3',5,5'-tetramethylbenzene hycrochlroride containing 0.03% $H_2O_2$ (2.5 mM) was added in each test, and reacted at 25° C. for 30 minutes. Then as a reaction stopper, 1 ml of a 1N aqueous solution of sulfuric acid was added to stop the enzyme reaction. Then, by using a spectrophotmeter, the absorption strength of this solution at a wavelength of 450 nm was measured. By plotting the absorption strength against the concentration of the standard substance from 0 to 20 ng/ml, the N/S ratio by the fraction of HRP standard antibody (the absorbance at an antigen concentratio of 0 ng/ml divided by the absorbancce at an antigen concentration of 20 ng/ml). The results are shown in Table 1.

TABLE 1

| | Measurement of human osteocalcin | | |
|---|---|---|---|
| Type of HRP-labelled antibody | OD$_{450}$ (osteocalcin 0 ng/ml) | OD$_{450}$ (osteocalcin 20 ng/ml) | N/S ratio (%) |
| IgG | 0.050 | 0.700 | 7.1 |
| F(ab')$_2$ | 0.040 | 0.630 | 6.3 |
| Fab' | 0.070 | 0.640 | 10.9 |

As shown in Table 1, the assay sensitivity varies depending upon the type of the HRP labelled antibody. Those obtained from F(ab')$_2$ and IgG had low background, and they clearly constituted systems having higher assay sensitivities.

Figure 4:
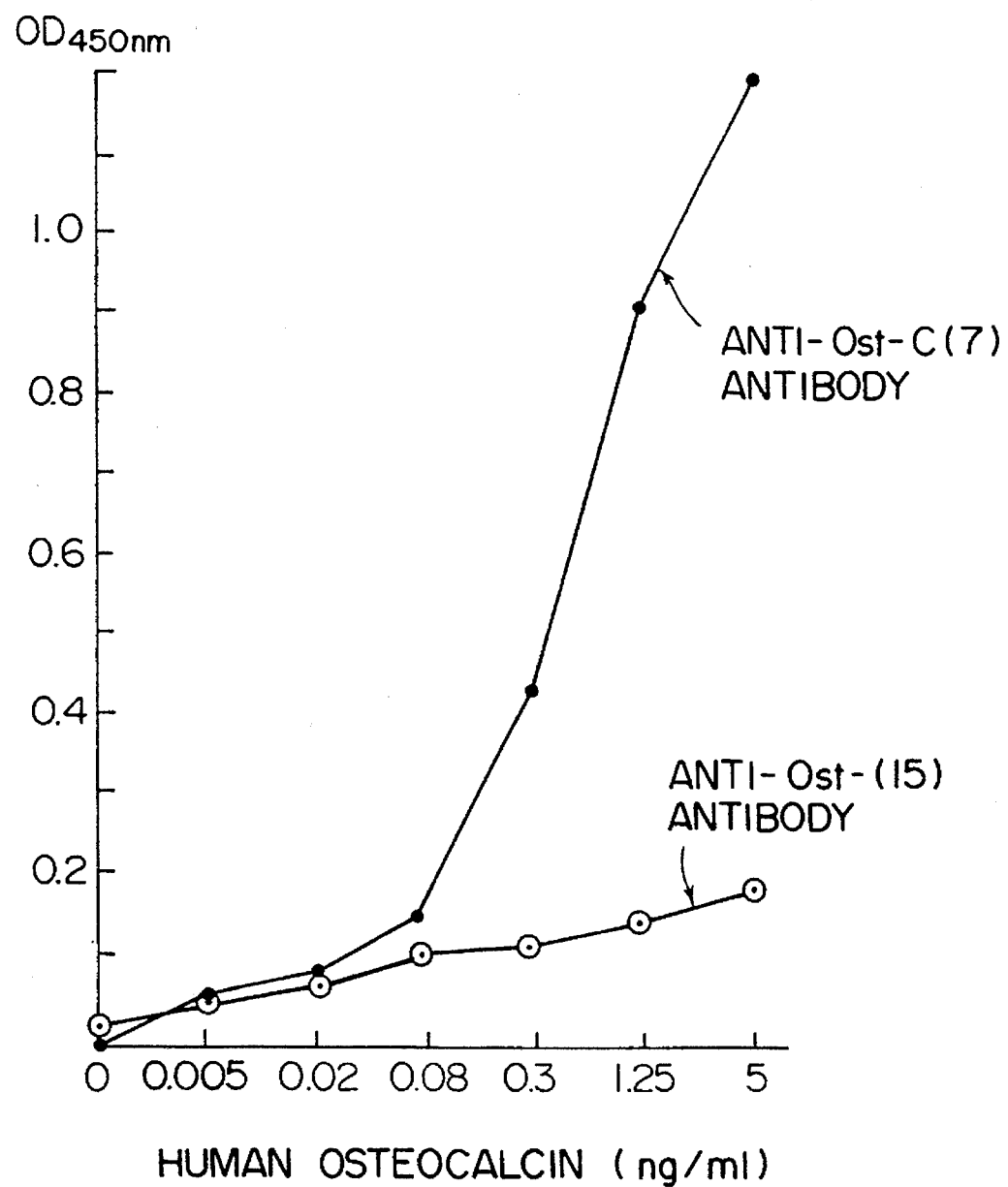
Figure 5:
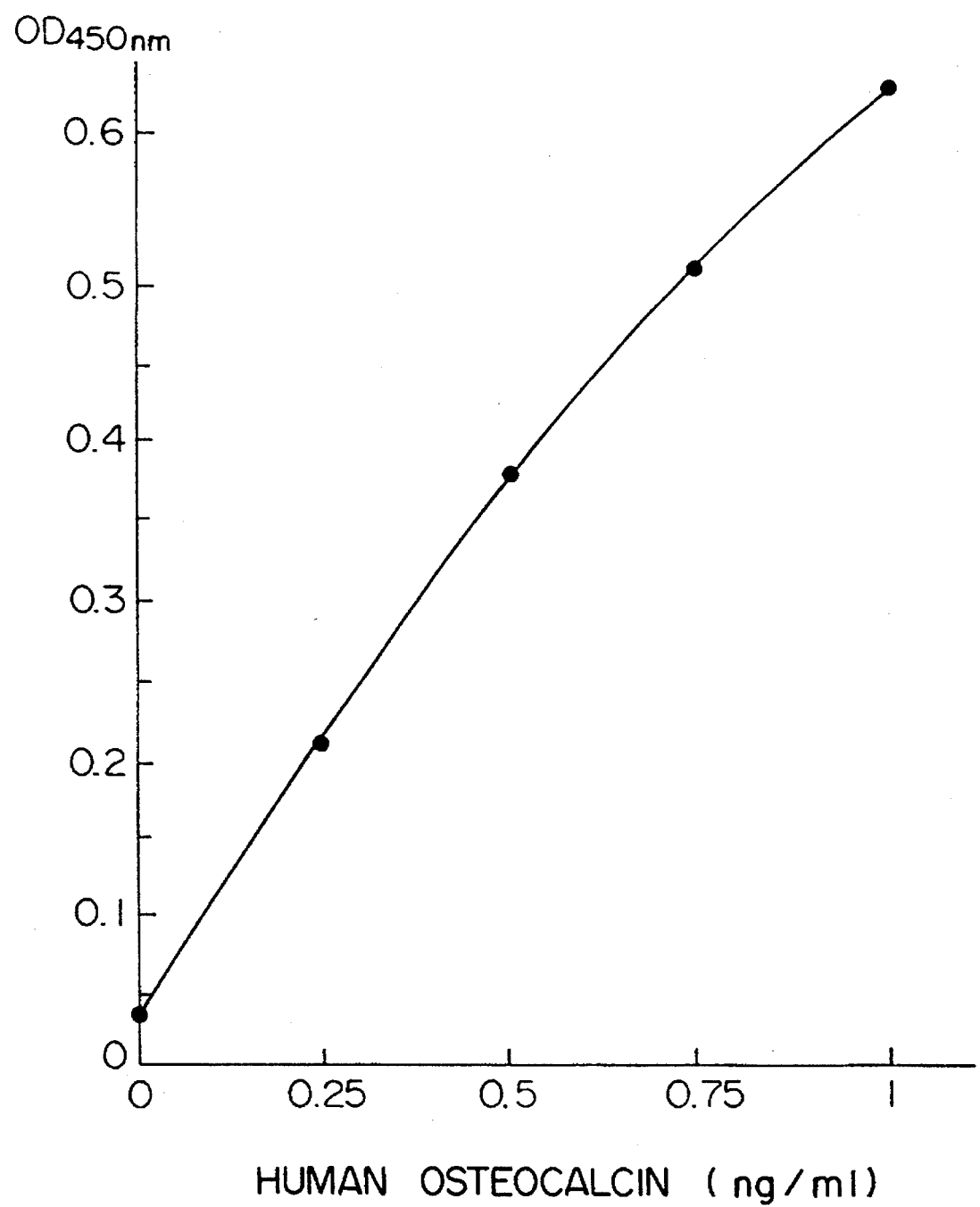
FIG. 5 shows the results of measurements when F(ab')₂ was used as a labelled antibody in Example 3.

The calibration curve prepared by using HRP-labelled antibody (F(ab')$_2$) is shown in FIG. 5.

Example 4

Studying of Specificity of Intact Molecules in the Intact Human Osteocalcin Assaying System (1)

Human osteocalcin (1 microgram/ml (0.1M Tris-HCl buffer, pH 8.0) was prepared in an amount of 1.7 ml, and 0.2 ml of each was prepared by using trypsin (human osteocalcin/trypsin, w/w ratio) in ratios of 1/2 (1), 1/1 (2), 2/1 (3), 10/1 (4), 50/1 (5) and 1/0 (6). The mixture was reacted at 25° C. for 60 minutes, and the reaction was stopped by using benzamidine. The reaction solutions were measured by using human osteocalcin assay system (I). The results are shown in Table 6. From the results of FIG. 6, it was seen that as the the conditions for cleavage of the untreated human osteocalcin with trypsin became rigorous, the amount of osteocalcin is converted to 0. This is considered to suggest the specificity of intact molecules of human osteocalcin.

Example 5

Studying of the Specificity of Intact Molecules of Intact Osteocalcin Assay System (1)

Human osteocalcin (99 ng) was dissolved in 300 microliters of 0.1M Tris-HCl (pH 8.0). By using trypsin (human osteocalcin:trypsin:trypsin=1:0.5 (w/w), the reaction was carried out at 25° C. for 60 minutes. The reaction was stopped by adding benzamidine.

The reaction solution was separated under the following conditions on inverse HPLC (ODS120T column).

Separating Conditions (i) Column: TSK-gel (Toso Col., Ltd. ODS-1207 (Lot 12T2H0257)

Figure 8:
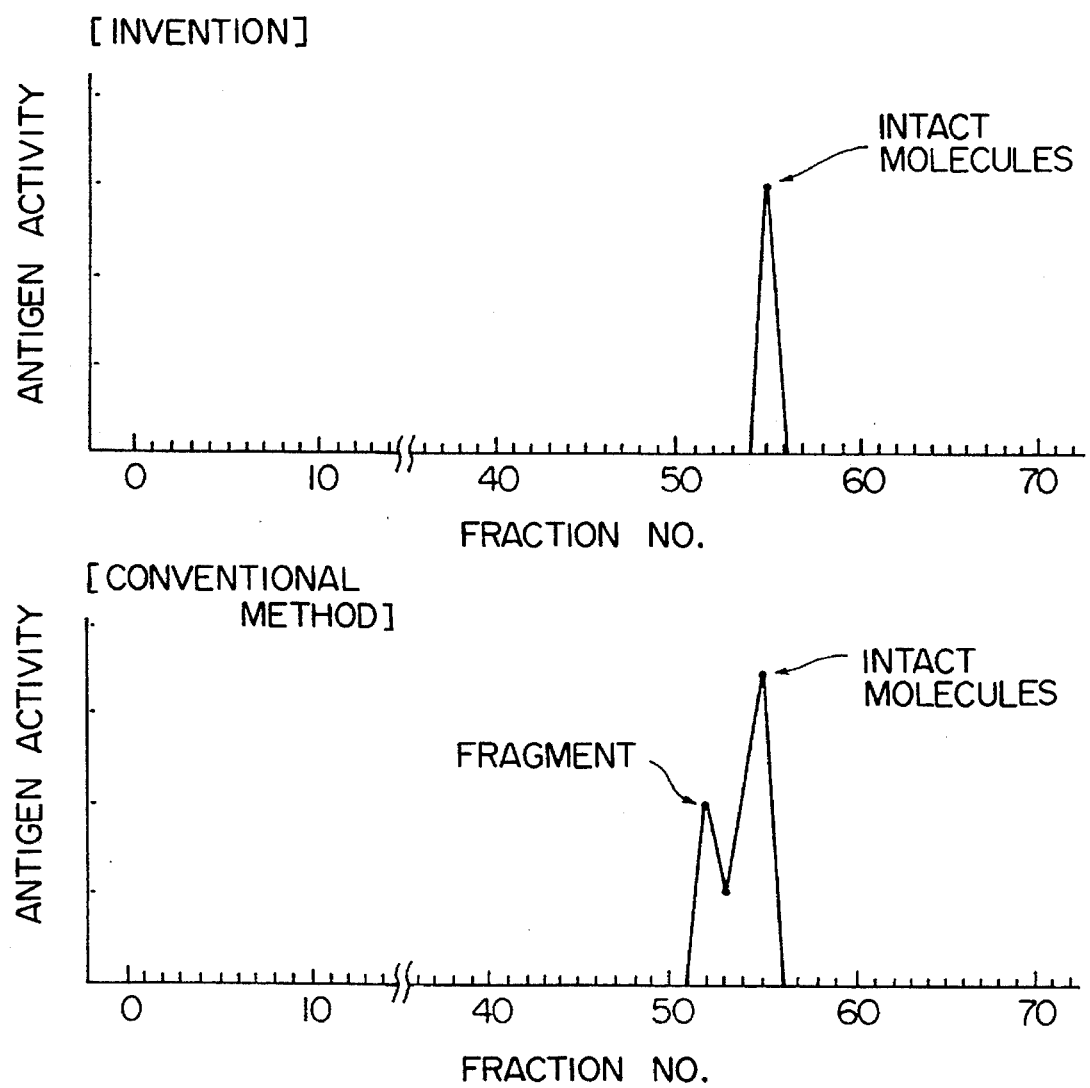
FIG. 8 shows the antigen activity of each fraction of human osteocalcin in Example 5.

(ii) Buffers solution A: 0.1% TFA/DW solution B: 80% acetonitrile, 0.1% TFA/DW (iii) Separation: A→B the gradient shown in FIG. 7 (OD 210 nm) 1 ml/min. Flow Each fraction, 1 ml, was sampled and the osteocalcin antigen activity of each fraction was measured by using the above intact human osteocalcin. The results are shown in FIG. 8 under "this invention". Only near this fraction No. 55, antigenic activity was seen, and the specificity of intact molecules of human osteocalcin was confirmed. The results obtained by measuring each fraction in the same direction was measured by the CIS kit made by Midori Jyuji Co., Ltd. are shown in FIG. 8 under "conventional method". The results show that the antigen activity existed not only near fraction No. 55 corresponding to intact molecules but also near fraction No. 52. From this, it was confirmed that the conventional method simultaneously measured not only intact molecules but also the fragment in an intermediate region. It is seen from -Δ-Δ that the measurement of a fragment by the conventional method is non-quantitative with respect to intact molecules.

Example 6

Measurement of Osteocalcin in a Human Serum Sample

By using the assay system (I) established in Example 3, the amount of human osteocalcin in the serum was measured on a patient of osteosarcoma.

Figure 9:
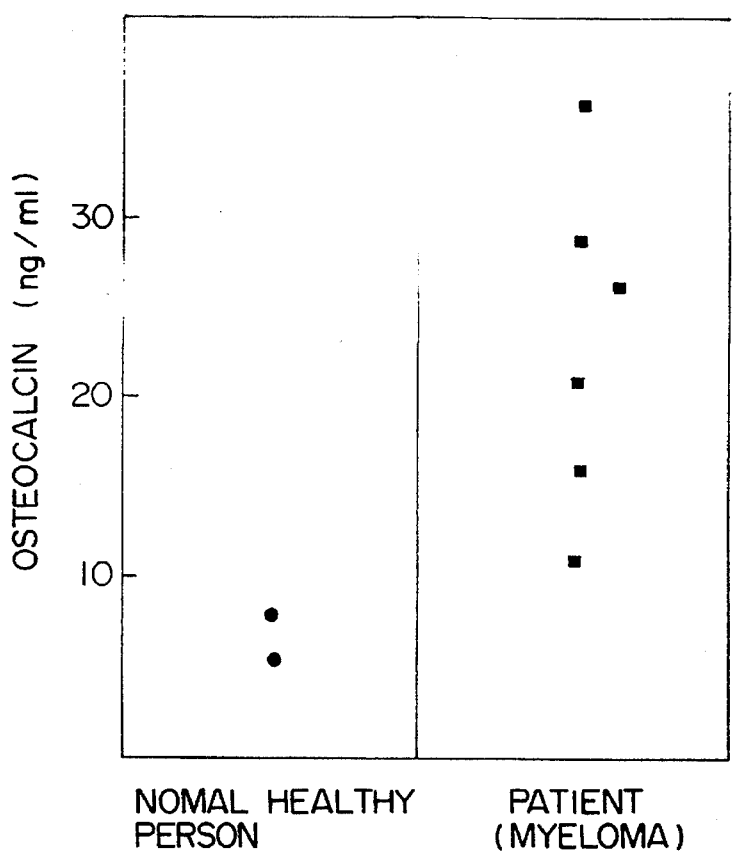
FIG. 9 shows the results of measurement of human osteocalcin in the sera of a normal healthy person and a patient of myeloma in Example 6.
Figure 10:
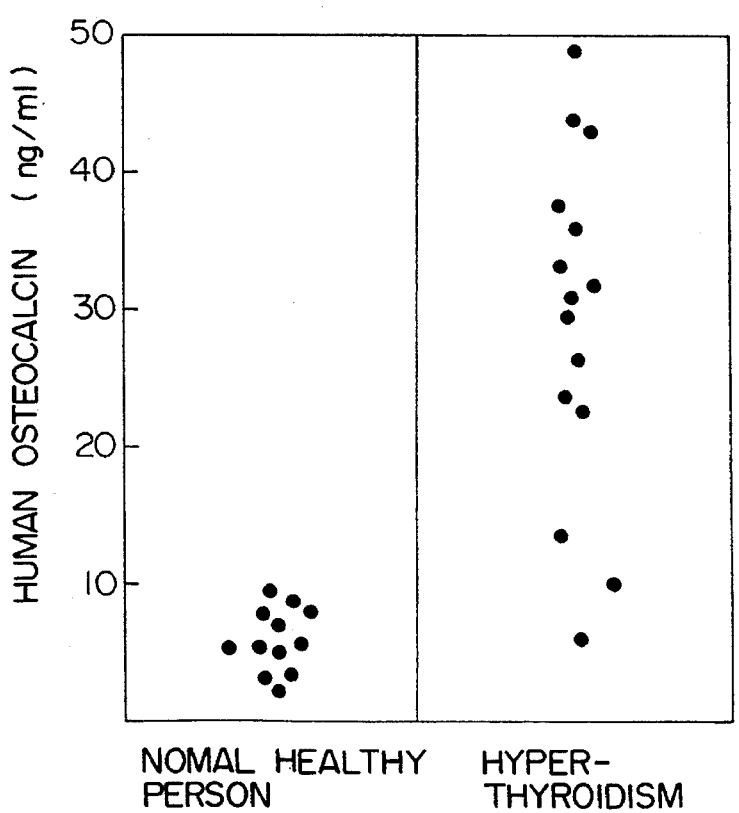
FIG. 10 shows the results of measurement of human osteocalcin in the plasma of a patient of hyper-parathyrodism in accordance with Example 10.

The results are shown in FIG. 9. The results clearly showed that the measured value on the patient was higher than that on a normal healthy person, and this assay method shows clearly that it can measure the amount of osteocalcin in an actual patient.

Example 7

Measurement of Osteocalcin in Human Plasma

By using the assay system (I) established by Example 3, the amount of human ostocalcin in the plasma was measured on a patient of parathyroidism. The results are shown in Table 10. They apparently showed that the measured values on the patient were higher than those on a normal healthy person.

Example 8

Structure of the Assay System (III) for Assaying the Total Amount of Intact Human Osteocalcin and its Fragment A PBS solution of 20 micrograms/ml of an IgG fragment of anti-Ost-N(20) antibody was prepared. Polystyrene balls (diameter 6.3 mm) were immersed in it to obtain anti-Ost-N(20) antibody-fixed polystyrene balls were obtained. On the other hand, an enzyme-labelled antibody, anti-Ost-N(20) antibody F(ab')$_2$, a peptide having 1 to 19 residues on the N-terminal of antigen (to be referred to as antigen peptide (N-19), which was prepared by varying the concentration, and the anti-Ost-N(20)-fixed styrene balls were added at the same time, and reacted for 2 hours at 37° C. After the reaction, the reaction system was washed three times with PBS, and a color reaction was carried out. The results are shown in FIG. 11. According to FIG. 11, variations occurred in $OD_{450nm}$ depending upon the amount of the antigenic peptide (N-19). Thus, there was obtained a possibility of assaying N-terminal fragment (N-19) of osteocalcin by the sandwich method.

Example 9

Preparation of Hybridoma for Producing a Monoclonal Antibody (1) Preparation of antigen-stimulated lymphocytes 90 micrograms of the Ost-N(20)-KLH bound product obtained in Example 1 (A) and (B) and an emulsion of a complete Freund's adjuvant were intraperitoneally administered to male Balb/c mice. Then five times at an interval of 3 to 4 weeks, an emulsion of 40 to 50 micrograms of Ost-N(20)-KLH bound product and incomplete Freund's adjuvant was intraperidonally administered. After five administrations, a solution of 60 micrograms of the Ost-N(20)-KLH bound product in 1.0 ml of physiological saline was intravenously administered. Four days later, the spleen was taken out aseptically from the mice. By passing through a stainless steel mesh, a suspension of the spleen cells in RPMI-1640 (made by Gibco Company) supplemented with 0.39 g/liter of L-glutamine, 0.2 g liter of kanamycin sulfate and 2.0 g/liter of $NaHCa_3$ was prepared. The floating cells were washed three times with the above medium to prepare a suspension of the spleen cells.
(2) Cell fusion Mouse myeloma cells P3U1 was cultivated in a GIT synthetic medium (a product of Daigo Eiyo Kagaku Co., Ltd.) supplemented with 0.2 g/liter of kanamycin sulfate. The myeloma cells were in the logarithmic period of cell division at the time of cell fusion. The spleen cells and the myeloma cells in a ratio of 3:1 were suspended in serum-free RPMI-1640 medium, and then centrifuged at 1300 arpm for 5 minutes. The above medium was removed. Then, 1 ml of a 50% polyethylene glycol Solution (pH 8.2) having an average molecular weight of 1,500 was gently added to the settled cells to form a suspension. Then, 9 ml of serum-free RPMI-1640 medium was added, and the cells were shaken carefully. Thereafter, for 5 minutes, the centrifugal separation was carried out at 1,000 rpm. The supernatant medium was removed, and the cells were collected as a precipitate and suspended in 40 ml of GIT medium.

(3) Obtaining of the cloned hybridoma

The fused cell suspension was distributed on a 96-well microtiter plate 200 microliters per well), and the plate was cultivated in an atmosphere containing 5% of $CO_2$ at 37° C. After 1 and 2 days, and thereafter, half of the amount of the medium was exchaged with a fresh GIT/HAT medium, and the cultivation was continued. After 11 days, screening was carried out by the enzyme immunosorbent method on antibodies to synthetic peptide ($^1$Tyr-$^{20}$Arg) in the supernatant liquid of hybridoma. The second antibody used was anti-goat-mouse IgG antibody labelled with alkaline phosphatase. Among 192 wells to which the hybridomas were distributed, 124 wells showed colonies of the fused cells. Among them, 8 wells were antibody-positive.

It was desired that the number of hybridomas in each antibody-positive well was 0.9 cell per well in the 96 well-microplate, and thymus cells of Balb/c mice were added as feeder cells and distibuted to the plate, and then cultivated in a GIT culture medium supplemented with kanamycin sulfate (0.2 g/liter). By observation under a microscope, single colonies were accurately formed. Antibodies to the synthetic peptide ($^1$Tyr-$^{20}$Arg) in the supernatant of the hybridomas were screened by the enzyme immunosorbent method. Each well was antibody-positive and produced anti-human osteocalcin monoclonal antibody.

As above, eight cloned hybridomas were obtained.

Example 10

Obtaining a Monoclonal Antibody (1) Cultivation of the Hybridomas

The cloned hybridomas obtained in Example 9 were intrapetitoneally administered at a cell number of $10^6$ to $10^7$/mouse to Balb/c mice to which 0.1 ml of pristan (Wako Pure chemical Co., Ltd.) had been given two weeks before. Then, on the 7 to 10 days, ascites were taken in an amount of 2 to 3 ml/mice.

(2) Purification of the monoclonal antibody

The ascites were purified by the method of Ey et al. (see P. L. Ey et al., Immunochemistry, 15, 429, 436 (1978). The ascites (2 to 3 ml) was caused to flow through a protein A-Sepnalose column (gel capacity 5 ml) equlibrated with 0.1M phosphate buffer. Then, 0.1M sodium citrate buffers having a pH of 6.0, 5.0, 4.0 and 3.0 were successively passed through the column to dilute the monoclonal antibody to obtain purified monoclonal antibodies.

(3) Class of the purified monoclonal antibodies

The specific of the purified monoclonal antibodies were determined by the Oocterloony gel disperion test by using class specific antimouse anti-sera. The results are shown in Table 2.

TABLE 2

| Antibody | $IgG_1$ | $IgG_2$ a | $IgG_2$ b | $IgG_3$ | IgM |
|---|---|---|---|---|---|
| Clon.-4F | + | | | | |
| Clon.-1G | | | + | | |
| Clon.-9G | | | + | | |
| Clon.-10B | + | | | | |
| Clon.-5E | + | | | | |
| Clon.-2A | | | + | | |
| Clon.-12E | | | | | + |
| Clon.-12F | | + | | | |

Example 11

Searching for the Identify and Difference of an Epitope in Monoclonal Antibodies The difference and identify of an epitope in monoclonal antibodies were searched by the binding inhibition assay described in Japan Immunology Handbook "Monoclonal Antibodies as Anti-tumor Antibodies ("Nippon Rinsho 1984 Spring Extra Issue).

A 20 microgram/ml PBS solution of a polyclonal antibody (anti-Ost-(7)) to the C-terminal peptide ($^{43}$Arg-$^{49}$Val) of human osteocalcin prepared in Example 2 was distributed to a 96-well microplate at a rate of 100 microliters/well, and-allowed to stand stationary overnight at 4° C. After washing with PBS, the washing solution 0.5% KBSA-PBS was added, and further maintained overnight, to prepare an anti-Ost-C (7)antibody-fixed plate. To this plate, 0.5% BSA-50 mM Tris-HCl buffer solution (pH 8) having a purified human osteocalcin in a concentration of 5 ng/ml was added to the plate at a rate of 100 microliters per well, and reacted at 25° C. for 1.5 hours, folllowed by washing with 50 mM Tris-HCl buffer.

Then, a 0.5% BSA-50 mM Tris-HCl buffer of human osteocalcin monoclonal antibody Clon-12F labelled with horse radish peroxidase (HRP) in a concentration of 1 microgram/l was added at a rate of 50 microliters of together with 0.5% BSA-50mM Tris-HCl buffer of each of various monoclonal antibodies having a concentration of 20 micrograms/ml simultaneously at a rate of 50 microliters per well, and reacted at 25° C. for 1.5 hours. After washing the wells with a 50 mM Tris-HCl buffer, 150 microliters of a substrate solution (pH 8) (containing 50 mg/dl of 2,2'-azino-di[3-ethylbenzothiazolinesulfonate-(6s)]) diammonium salt and 50 microliters/dl of 2M $H_2O_2$ in 0.1M phosphate/citrate buffer (pH 4.5) to induce coloration at 25° C. for 6 minutes. 50 microliters of a 0.1M aqueous solution of oxalic acid was added to stop the reaction. The absorbance was measured at 415 nm by a plate reader. The results are shown in Table 3.

From the results shown in Table 3, it is seen that among the 9 monoclonal antibodies obtained in Example 6, Clon-4F and Clon-12F are not inhibited by Clon-9G, Clon-10kB and Clon-12E. Therefore, evidently, they recognize different epitopes from these monoclonal antibodies. Furthermore, Clon-5E, Clon-2A and Clon-12F have the same epitope or epitopes close to each other, and these antibodies cannot simultaneously bind to them.

As control, anti-GST (glutathione) antibody was used.

The hybridoma 10B that produces monoclonal antibody 10B has been deposited under the Budapest Treaty at the Fermentation Research Institute, Agency of Industrial Science and Technology, 1–3, Higashi 1-chome, Tsukuba-shi, Ibaraki-ken 305, Japan on Aug. 28, 1991 and bears deposit number FERM BP-3538.

TABLE 3

| Unlabelled antibody | HRP-labelled antibody | Absorbance |
| --- | --- | --- |
| Clon-4F | Clon-12F | 0.185 |
| Clon-9G | | 0.180 |
| Clon-10B | | 0.103 |
| Clon-5E | | 0.058 |
| Clon-2A | | 0.040 |
| Clon-12E | | 0.175 |
| Clon-12F | | 0.072 |
| Control anti-GST antibody | | 0.174 |

Example 12

An Assaying System (I) Using Intact Human Osteocalcin Monoclonal Antibody (1) Preparation of antibody-fixed beads Polystyrene beads (6 mm in diameter) were well washed, and then allowed to stand for one day at 4° C. in a PBS solution of the monoclonal antibody Clon-10B obtained in Example 10 having a concentration of 20 micrograms/ml. Then, the beads were washed with PBS and allowed to stand for one day at 4° C. in a PBS solution of 1% bovine serum albumin (BSA) to subject them to a post coating treatment. Clon-10B antibody-fixed beads were obtained.

(2) Preparation of a HRP-labelled antibody

To 1 ml of a PBS solution containing 20 mg/ml of polyclonal antibody (anti-Ost-C(7)) to the C terminal side ($^{43}$Arg-$^{49}$Val) of human osteocalcin prepared in Example 2 were added 100 microliters of 1M acetate buffer (pH 4.2) and a solution of 40 microliters of pepsin in 20 microliters of the same buffer, and the reaction was carried out at 37° C. for 4 hours.

After the reaction, the reaction product was separated by using a Sephadex G 25 column (2 cm×45 cm) equilibrated with PBS to collect F(ab")$_2$. 50 microliters of a dimethylformamide solution of MBS in a concentration of 10 mg/ml was added to 2 ml of F(ab')$_2$ in 0.01M phosphate 0.15M NaCl (pH 7.4) solution in a concentration of 1 mg/ml, and the reaction was performed at 25° C. for 30 minutes. Then by using a column filled with Sephadex G-25, gel filtration was carried out using 0.1M phosphate buffer (0.1 MPB) (pH 6.0) to separate the MBS-acylated antibody from the unreacted MBS.

On the other hand, 120 microliters of a 60 mg/ml acetylmercaptosuccinyl anhydride in dimethyl formamide was added to 2 ml of a solution of 10 mg/ml of HRP in 0.1 MPB (pH 6.5), and they were reacted at 25° C. for 2 hours. Then 800 microliters of 0.1M Tris-HCl buffer (pH 7.0), 160 microliters of 0.1M EDTA, and 1.5 ml of 1M hydroxylamine were added, and reacted at 0° C. for 4 minutes. Then, the reaction solution was put into a collodion bag, and by using a solution containing 0.1 MPB (pH 6.0) and 4 mM EDTA, was dialyzed at 4° C. for 3 days to obtain a thiolated HRP.

Then, 2 mg of maleimidized antibody was mixed with 4 mg of mercaptosuccinyl HRP and the mixture was concentrated under ice cooling by using a collodion bag until the protein concentration became 4 to 10 mg/ml, and then, the mixed solution was allowed to stand overnight at 15° to 20° C. The liquid was gel-filtrated with a column filled with ultrogel AcA44 (LKB company) to obtain HRP-labelled anti-Ost-C(7) antibody.

(3) Sandwich EIA assay system

To each test tube were added one Clon-10B antibody-fixed bead prepared in (1), 200 microliters of 1% BSA-containing 0.05M TBS (pH 8.0)containing 0 to 20 ng/ml of the purified human osteocalcin (standard substance) and 200 microliters of 1% BSA-containing 0.05M TBS (pH 8.0) of HRP-labelled antibody prepared in (2) above, and incubated at 25° C. for 2 hours. Then, the solution in the test tube was removed by suction. Then after the test tube was washed with 0.05M TBS (pH 8.0), 0.1M phosphate/citrate buffer (pH 4.3) containing 0.02% H$_2$O$_2$ (2.5 mM) was added to each test tube, and at 25° C. for 30 minutes. As a reaction stopper, 1 ml of 1N aqueous sulfuric acid solution was added to stop the enzyme reaction. Then, by using this solution, the absorption strength at 450 nm was measured by using a spectrophotometer. By plotting this strength against the concentration of the standard substance (0 to 20 ng/ml, a calibration curve was prepared as shown in FIG. 12. From the results, it is seen that by using the method of assay in accordance with this invention, measurement could be made with a good accuracy up to 0.05 ng/ml.

Example 13

Studying of the Specificity

By using the assaying system constructed in Example 12, bovine osteocalcin (10.5, 2.5, 1.25 Ng/ml) was measured, and in accordance with the following computing formula, the cross reactivity was calculated. As a solid-phase antibody, Clon-10B, 2A, 12E and 12F and The polyclonal antibody (PCA) to N-terminal peptide ($^1$Tyr-$^{20}$Arg) of human osteocalcin were used in a predetermined concentration each.

Cross reactivity (%) = +

$$\left[ \frac{\begin{array}{c}\text{Concentration of human}\\\text{osteocalcin which gives}\\\text{the same absorbance}\\\text{as bovine osteocalcin}\\(10 \text{ ng/ml})\end{array}}{10 \text{ ng/ml}} \frac{\begin{array}{c}\text{Concentration of human}\\\text{osteocalcin which gives}\\\text{the same absorbance}\\\text{as bovine osteocalcin}\\(5 \text{ ng/ml})\end{array}}{5 \text{ ng/ml}} \right] /2 \times 100$$

The results are shown in Table 4.

TABLE 4

| Type of antibody | Cross reactivity (%) |
| --- | --- |
| MCA | |
| Clon-10B | 28.5 |
| Clon-2A | 42.5 |
| Clon-12E | 40.0 |
| Clon-12F | 14.0 |
| PCAāN(20) | 9.0 |

Example 14

Figure 13:
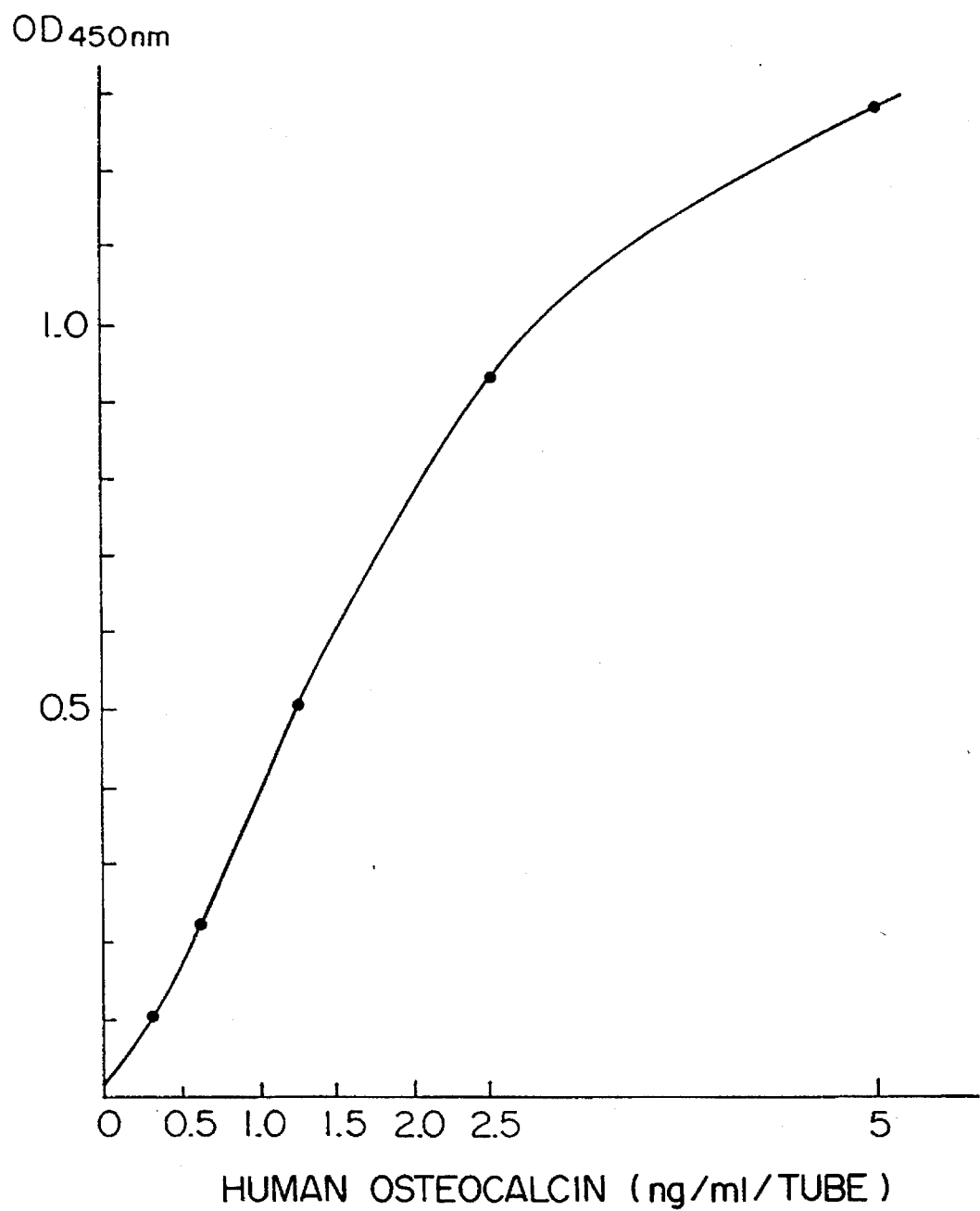

Assay System (II) for Assaying the Total Amount of Intact Human Osteocalcin and its Fragment by Using Monoclonal Antibody By using the beads to which was fixed a monoclonal antibody Clon-10B to the N-terminal peptide ($^1$Tyr-$^{20}$Arg) prepared in Example 11, HRP-labelled Ost-N(20) antibody prepared as in Example 11 by using the polyclonal antibody Ost-N(20) to the N-terminal peptide of human osteocalcin ($^1$Tyr-$^{20}$Arg) of human osteocalcin prepared in Example 1, and a solution containing 0 to 9 ng/ml of the N-terminal peptide ($^1$Tyr-$^{20}$Arg) of human osteocalcin, the relation between the concentration of the N-terminal peptide and the absorbance was determined by the same method as in Example 6, and is shown in FIG. 13. From the results, it is seen that by using the method of this invention, N-terminal fragment of human osteocalcin can be measured with good accuracy to an extent of 0.02 ng/ml.

Example 15

Studying (1) of Molecule Specificity by the Assaying System (II)

1.7 ml of a solution of human osteocalcin (1 microgram/ml in 0.1M Tris buffer (pH 8.0) was prepared, and then 0.2 ml of the solution was prepared into the following solutions using trypsin. Human osteocalcin/trypsin (w/W ratios: 1/2 (1), 1/1 (2), 2/1 (3), 10/1 (4), 30/1 (5), and 1/0 (6)). Then, each was reacted at 25° C. for 60 minutes, and the reaction was stopped by using benzamidine. The resulting reaction solutions were assayed by using the assaying system (II). The results are shown in FIG. 6 as ... 0 ... as fragment assaying systems.

It is clear from the foregoing that the present assaying system (II) reflect tha total amount of the intact molecules and the N-terminal fragment.

Example 16

Studying (2) of of Molecule Specificity by the Assaying System (II)

90 ng of human osteocalcin was disssolved in 200 microliters of 0.1M Tris buffer (pH 8.0), By using trypsin (human osteocalcin:trypsin=1:0.5 (w/w)), the reaction was carried out at 25° C. for 60 minutes and the reaction was stopped by using benzamidine. The reaction solution was subjected to the separating operation under the same conditions as in Example 5 by using reverse phase HPLC (ODS120T column). After separation, the osteocalcin antigen activity of each fraction was measured with the assaying system II (Example 14). The results are shown in FIG. 14.

From the results of FIG. (14), it became evident that the present assaying system (II) can assay the total amount of intact molecules and N-terminal fragment (N-19).

Example 17

Assaying of Osteocalcin Levels in Serum Samples of Patients with Renal Failure and Osteoprosis Assay Sample in Accordance with the Assaying Sample (II)

By the technique of Example 14, osteocalcin in assaying samples of patients (kidney disease and osteoporosis) of were measured.

The results are shown in FIG. 15. As shown, high values were observed in samples taken from patients with kidney disease and osteoporosis.

Then from the patients' samples showing high values, N-terminal fragments were separated and purified by inverse phase high velocity liquid chromatography. The fraction was examined by an amino acid sequenser, and it was confirmed that the fraction was an N-terminal fragment of $^1$Trr-$^{19}$Arg. this agreed with that shown by Caren M. Gundberg et al. (J. Clin. Intest. 77, 1762 (1986)).

In the above measured values, the fragment in the patient's serum was calculated by the following formula.

Measured value of the N-terminal fragment=the measured value by the assaying system (II)–the measured value by the assaying system (I)

Example 18

Studying of the Clinical Significance of the Measured Value of the Fragment

By using the assaying systems (I) and (II), the therapeutic agent in osteoporosis was evaluated with a group before treatment (n-15), groups under therapy (calcitonin administered (n=3); estrogen administered (n=4), and the average of the assayed values of fragment/the assay values of complete molecules were shown in Table 16. The calcitonin and estrogen were both bone resorption inhibitors. The results given in FIG. 16 show that the treatment with these drugs showed a decreasing tendency in the ratio of the measured value of the fragment/measured values of complete molecules. Thus, the measured value on the fragment suuggested a possibility of showing bone resorption activity. Furthermore, the estrogen-administered group showed superiority at a risk of 10% as compared before treatment.

We claim:

1. A method of immunologically assaying intact human osteocalcin in a human sample, which comprises the steps of:
   bringing the sample into contact with a solid-phase antibody and a labelled antibody,
   reacting the sample with the solid-phase and labelled antibodies so as to form a complex of the labelled antibody—intact human osteocalcin—solid-phase antibody in the human sample,
   separating the complex from unbound labelled antibody,
   measuring the amount of the labelled antibody in the complex, and
   correlating the amount of the labelled antibody in the complex with the amount of intact human osteocalcin in the sample, wherein
   (1) one of the antibodies is an antibody or antibody fragment to human osteocalcin which specifically binds to an epitope within a region of amino acids 1 to 20 of the N-terminal of human osteocalcin, and
   (2) the other antibody is an antibody or antibody fragment to human osteocalcin which specifically binds to an epitope within a region of amino acids 43 to 49 of the C-terminal of human osteocalcin.

2. The method of claim 1 wherein the antibody which specifically binds to the N-terminal of human osteocalcin is a polyclonal antibody or polyclonal antibody fragment.

3. The method of claim 1 wherein the antibody which specifically binds to the N-terminal of human osteocalcin is a monoclonal antibody or monoclonal antibody fragment.

4. The method of any one of claims 1 to 3 wherein the antibody which specifically binds to the C-terminal of human osteocalcin is a polyclonal antibody or polyclonal antibody fragment.

5. The method of claim 1 wherein the antibodies which specifically bind to the N-terminal and C-terminal of human osteocalcin are both polyclonal antibodies or polyclonal antibody fragments.

6. The method of claim 1 wherein the antibody which specifically binds to the C-terminal of human osteocalcin is a monoclonal antibody or monoclonal antibody fragment.

7. The method of claim 1 wherein the labelled antibody is a Fab' or F(ab')$_2$ fragment.

8. The method of claim 1 wherein the solid-phase antibody is bound to a plastic bead having a smooth surface having a centerline average roughness (Ra) of not more than 1.5 micrometers.

9. The method of claim 1 wherein the human sample is serum, plasma, or urine.

10. The method of claim 1 wherein the solid-phase antibody is a polyclonal antibody or polyclonal F(ab')$_2$ fragment to human osteocalcin, and wherein the labelled antibody is a polyclonal antibody or polyclonal F(ab')$_2$ fragment to human osteocalcin.

11. A kit for immunologically assaying intact human osteocalcin in a human sample comprising a solid-phase antibody and a labelled antibody, wherein
   (1) one of the antibodies is an antibody or antibody fragment to human osteocalcin which specifically binds to an epitope within a region of amino acids 1 to 20 of the N-terminal of human osteocalcin, and
   (2) the other antibody is an antibody or antibody fragment to human osteocalcin which specifically binds to an epitope within a region of amino acids 43 to 49 of the C-terminal of human osteocalcin.

12. A kit for immunologically assaying intact human osteocalcin comprising in combination:
   (a) a solid-phase antibody,
   (b) a labelled antibody,
   (c) a dilution buffer, and
   (d) a washing agent,
   wherein
   (1) one of the antibodies is an antibody or antibody fragment to human osteocalcin which specifically binds to an epitope within a region of amino acids 1 to 20 of the N-terminal of human osteocalcin, and
   (2) the other antibody is an antibody or antibody fragment to human osteocalcin which specifically binds to an epitope within a region of amino acids 43 to 49 of the C-terminal of human osteocalcin.

13. The kit according to claim 12, wherein the labelled antibody is an antibody labelled with an enzyme, and wherein the kit further includes a substrate for measuring the enzyme activity and a reaction stopping agent.

\* \* \* \* \*